(12) United States Patent
Cleary et al.

(10) Patent No.: US 8,481,059 B2
(45) Date of Patent: Jul. 9, 2013

(54) HYDROGEL COMPOSITIONS

(75) Inventors: Gary W. Cleary, Los Altos Hills, CA (US); Shoreh Parandoosh, Menlo Park, CA (US); Mikhail M. Feldstein, Moscow (RU); Anatoly E. Chalykh, Moscow (RU); Nicolai A. Platé, Moscow (RU); Valery G. Kulichikhin, Moscow (RU)

(73) Assignees: A.V. Topchiev Institute of Petrochemical Synthesis, Russian Academy of Sciences, Moscow (RU); Corium International, Inc., Menlo Park, CA (US)

( * ) Notice: Subject to any disclaimer, the term of this patent is extended or adjusted under 35 U.S.C. 154(b) by 255 days.

(21) Appl. No.: 12/491,088

(22) Filed: Jun. 24, 2009

(65) Prior Publication Data

US 2009/0258060 A1 Oct. 15, 2009

Related U.S. Application Data

(62) Division of application No. 10/137,664, filed on May 1, 2002.

(60) Provisional application No. 60/288,008, filed on May 1, 2001.

(51) Int. Cl.
*A61K 9/00* (2006.01)
*C08G 61/04* (2006.01)

(52) U.S. Cl.
USPC .................................. 424/400; 520/916

(58) Field of Classification Search
None
See application file for complete search history.

(56) References Cited

U.S. PATENT DOCUMENTS

| 2,561,071 A | 7/1951 | Prisk |
| 2,579,403 A | 12/1951 | Slomowitz et al. |

(Continued)

FOREIGN PATENT DOCUMENTS

| CA | 2520986 | 4/2000 |
| CA | 2402021 | 9/2001 |

(Continued)

OTHER PUBLICATIONS

Barbucci et al. "Swelling Behavior of Carboxymethylcellulose Hydrogels in Relation to Cross-Linking, pH, and Charge Density"; Macromolecules, vol. 33, No. 20, 2000.*

(Continued)

*Primary Examiner* — Isis Ghali
(74) *Attorney, Agent, or Firm* — Susan T. Evans; Judy M. Mohr; McDermott Will & Emery LLP

(57) ABSTRACT

Hydrogel compositions are provided (a) that have a continuous hydrophobic phase and a discontinuous hydrophilic phase, (b) that have a discontinuous hydrophilic phase and a continuous hydrophilic phase, or (c) that are entirely composed of a continuous hydrophilic phase. The hydrophobic phase, if present, is composed of a hydrophobic polymer, particularly a hydrophobic pressure-sensitive adhesive (PSA), a plasticizing elastomer, a tackifying resin, and an optional antioxidant. The discontinuous hydrophilic phase, if present, is composed of a crosslinked hydrophilic polymer, particularly a crosslinked cellulosic polymer such as crosslinked sodium carboxymethylcellulose. For those hydrogel compositions containing a continuous hydrophilic phase, the components of the phase include a cellulose ester composition or an acrylate polymer or copolymer, and a blend of a hydrophilic polymer and a complementary oligomer capable of hydrogen bonding thereto. Films prepared from hydrogel compositions containing or entirely composed of the aforementioned continuous hydrophilic phase can be made translucent, and may be prepared using either melt extrusion or solution casting. A preferred use of the hydrogel compositions is in wound dressings, although numerous other uses are possible as well.

22 Claims, 2 Drawing Sheets

U.S. PATENT DOCUMENTS

| | | |
|---|---|---|
| 3,150,977 A | 9/1964 | Hart et al. |
| 3,689,439 A | 9/1972 | Field et al. |
| 3,721,657 A | 3/1973 | Seiderman |
| 3,749,755 A | 7/1973 | Bronstart et al. |
| 3,852,228 A | 12/1974 | Brothers |
| 3,957,605 A | 5/1976 | Assarsson et al. |
| 3,993,551 A | 11/1976 | Assarsson et al. |
| 3,996,934 A | 12/1976 | Zaffaroni |
| 4,091,090 A | 5/1978 | Sipos |
| 4,093,673 A | 6/1978 | Chang et al. |
| 4,160,020 A | 7/1979 | Ayer et al. |
| 4,231,369 A | 11/1980 | Sorensen et al. |
| 4,277,580 A | 7/1981 | Allen et al. |
| 4,325,851 A | 4/1982 | Colon et al. |
| 4,346,709 A | 8/1982 | Schmitt et al. |
| 4,367,732 A | 1/1983 | Poulsen et al. |
| 4,492,685 A | 1/1985 | Keith et al. |
| 4,529,601 A | 7/1985 | Broberg et al. |
| 4,552,751 A | 11/1985 | Inaba et al. |
| 4,557,934 A | 12/1985 | Cooper |
| 4,562,060 A | 12/1985 | Broberg et al. |
| 4,568,343 A | 2/1986 | Leeper et al. |
| 4,587,289 A | 5/1986 | Comert et al. |
| 4,593,053 A | 6/1986 | Jevne et al. |
| 4,624,665 A | 11/1986 | Nuwayser |
| 4,699,146 A | 10/1987 | Sieverding |
| 4,713,243 A | 12/1987 | Schiraldi et al. |
| 4,743,249 A | 5/1988 | Loveland |
| 4,750,482 A | 6/1988 | Sieverding |
| 4,771,105 A | 9/1988 | Shirai et al. |
| 4,849,224 A | 7/1989 | Chang et al. |
| 4,863,738 A | 9/1989 | Taskovich |
| 4,863,970 A | 9/1989 | Patel et al. |
| 4,867,748 A | 9/1989 | Samuelsen |
| 4,871,536 A | 10/1989 | Arraudeau et al. |
| 4,873,299 A | 10/1989 | Nowakowsky et al. |
| 4,877,628 A | 10/1989 | Stypula |
| 4,904,247 A | 2/1990 | Therriault et al. |
| 4,906,169 A | 3/1990 | Chien et al. |
| 4,927,408 A | 5/1990 | Haak et al. |
| 4,945,084 A | 7/1990 | Packman |
| 4,953,053 A | 8/1990 | Pratt |
| 4,973,468 A | 11/1990 | Chiang et al. |
| 4,983,395 A | 1/1991 | Chang et al. |
| 5,023,084 A | 6/1991 | Chien et al. |
| 5,053,227 A | 10/1991 | Chiang et al. |
| 5,057,500 A | 10/1991 | Thornfeldt |
| 5,073,381 A | 12/1991 | Ivan et al. |
| 5,102,662 A | 4/1992 | Gallagher |
| 5,125,894 A | 6/1992 | Phipps et al. |
| 5,133,970 A | 7/1992 | Petereit et al. |
| 5,141,750 A | 8/1992 | Lee et al. |
| 5,173,302 A | 12/1992 | Holmblad et al. |
| 5,183,901 A | 2/1993 | Login et al. |
| 5,196,405 A | 3/1993 | Packman |
| 5,200,190 A | 4/1993 | Azuma et al. |
| 5,206,385 A | 4/1993 | Login et al. |
| 5,224,928 A | 7/1993 | Sibalis et al. |
| 5,232,702 A | 8/1993 | Pfister et al. |
| 5,234,690 A | 8/1993 | Chiang et al. |
| 5,234,957 A | 8/1993 | Mantelle |
| 5,240,995 A | 8/1993 | Gyory et al. |
| 5,254,346 A | 10/1993 | Tucker et al. |
| 5,270,358 A | 12/1993 | Asmus |
| 5,276,079 A | 1/1994 | Duan et al. |
| 5,296,512 A | 3/1994 | Beier et al. |
| 5,300,291 A | 4/1994 | Sablotsky et al. |
| 5,310,563 A | 5/1994 | Curtis et al. |
| 5,322,689 A | 6/1994 | Hughes et al. |
| 5,326,685 A | 7/1994 | Gaglio et al. |
| 5,332,576 A | 7/1994 | Mantelle |
| 5,338,490 A | 8/1994 | Dietz et al. |
| 5,342,623 A | 8/1994 | Enscore et al. |
| 5,344,394 A | 9/1994 | Gyory et al. |
| 5,354,823 A | 10/1994 | Tseng et al. |
| 5,362,420 A | 11/1994 | Itoh et al. |
| 5,376,377 A | 12/1994 | Gale et al. |
| 5,422,119 A | 6/1995 | Casper |
| 5,438,076 A | 8/1995 | Friedman et al. |
| 5,446,070 A | 8/1995 | Mantelle |
| 5,456,745 A | 10/1995 | Roreger et al. |
| 5,462,743 A | 10/1995 | Turner et al. |
| 5,462,745 A | 10/1995 | Enscore et al. |
| 5,492,943 A | 2/1996 | Stempel |
| 5,508,024 A | 4/1996 | Tranner |
| 5,508,367 A | 4/1996 | Zajaczkowski |
| 5,527,271 A | 6/1996 | Shah et al. |
| 5,543,148 A | 8/1996 | Lapidus |
| 5,563,153 A | 10/1996 | Mueller et al. |
| 5,575,654 A | 11/1996 | Fontenot |
| 5,593,686 A | 1/1997 | Kissel et al. |
| 5,594,068 A | 1/1997 | Buchanan et al. |
| 5,599,373 A | 2/1997 | Zanuccoli |
| 5,614,178 A | 3/1997 | Bloom et al. |
| 5,631,267 A | 5/1997 | Gliech et al. |
| 5,633,010 A | 5/1997 | Chen |
| 5,641,504 A | 6/1997 | Lee et al. |
| 5,641,507 A | 6/1997 | DeVillez |
| 5,643,187 A | 7/1997 | Naestoft et al. |
| 5,645,062 A | 7/1997 | Anderson et al. |
| 5,645,855 A | 7/1997 | Lorenz |
| 5,656,286 A | 8/1997 | Miranda et al. |
| 5,660,178 A | 8/1997 | Kantner et al. |
| 5,662,925 A | 9/1997 | Ebert et al. |
| 5,663,010 A | 9/1997 | Stocchiero |
| 5,674,561 A | 10/1997 | Dietz et al. |
| 5,700,478 A | 12/1997 | Biegajski et al. |
| 5,702,721 A | 12/1997 | Horstmann et al. |
| 5,718,187 A | 2/1998 | Pollock et al. |
| 5,718,886 A | 2/1998 | Pellico |
| 5,719,197 A | 2/1998 | Kanios et al. |
| 5,723,145 A | 3/1998 | Shikinami et al. |
| 5,725,876 A | 3/1998 | Mantelle et al. |
| 5,726,250 A | 3/1998 | Zajaczkowski |
| 5,730,999 A | 3/1998 | Lehmann et al. |
| 5,744,155 A | 4/1998 | Freidman et al. |
| 5,762,956 A | 6/1998 | Chien |
| 5,770,220 A | 6/1998 | Meconi et al. |
| 5,773,490 A | 6/1998 | Shikinami et al. |
| 5,780,050 A | 7/1998 | Jain et al. |
| 5,785,527 A | 7/1998 | Jensen et al. |
| 5,785,976 A | 7/1998 | Westesen et al. |
| 5,788,983 A | 8/1998 | Chien et al. |
| 5,800,832 A | 9/1998 | Tapolsky et al. |
| 5,804,611 A | 9/1998 | Takoh et al. |
| 5,827,213 A * | 10/1998 | Jensen ........................... 602/62 |
| 5,827,525 A | 10/1998 | Liao et al. |
| 5,830,932 A | 11/1998 | Kay |
| 5,837,713 A | 11/1998 | Gliech |
| 5,843,472 A | 12/1998 | Ma et al. |
| 5,846,558 A | 12/1998 | Nielsen et al. |
| 5,851,549 A | 12/1998 | Svec |
| 5,853,755 A | 12/1998 | Foldvari |
| 5,858,332 A | 1/1999 | Jensen et al. |
| 5,858,410 A | 1/1999 | Muller et al. |
| 5,863,662 A | 1/1999 | Hornby et al. |
| 5,876,746 A | 3/1999 | Jona et al. |
| 5,879,691 A | 3/1999 | Sagel et al. |
| 5,879,701 A | 3/1999 | Audett et al. |
| 5,891,453 A | 4/1999 | Sagel et al. |
| 5,894,017 A | 4/1999 | Sagel et al. |
| 5,900,249 A | 5/1999 | Smith |
| 5,902,598 A | 5/1999 | Chen et al. |
| 5,911,980 A | 6/1999 | Samour et al. |
| 5,912,271 A | 6/1999 | Brodine et al. |
| 5,916,587 A | 6/1999 | Min et al. |
| 5,942,543 A | 8/1999 | Ernst |
| 5,945,032 A | 8/1999 | Breitenbach et al. |
| 5,945,457 A | 8/1999 | Plate et al. |
| 5,948,416 A | 9/1999 | Wagner et al. |
| 5,948,430 A | 9/1999 | Zerbe et al. |
| 5,948,433 A | 9/1999 | Burton et al. |
| 5,958,379 A | 9/1999 | Regenold et al. |
| 5,958,446 A | 9/1999 | Miranda et al. |
| 5,962,011 A | 10/1999 | DeVillez |
| 5,972,377 A | 10/1999 | Jona et al. |
| 5,976,565 A | 11/1999 | Fotinos |

| | | | | | | |
|---|---|---|---|---|---|---|
| 5,985,311 | A | 11/1999 | Cordes et al. | 6,805,874 B1 | 10/2004 | Lutz et al. |
| 5,985,860 | A | 11/1999 | Toppo | 6,806,308 B2 | 10/2004 | Zajac |
| 5,985,990 | A | 11/1999 | Kantner et al. | 6,884,833 B2 | 4/2005 | Cheang et al. |
| 5,989,569 | A | 11/1999 | Dirksing et al. | 6,946,142 B2 | 9/2005 | Chang et al. |
| 5,990,179 | A | 11/1999 | Gyori et al. | 6,962,691 B1 | 11/2005 | Lulla et al. |
| 5,993,836 | A | 11/1999 | Castillo | 7,078,359 B2 * | 7/2006 | Stepanian et al. .............. 442/59 |
| 5,993,849 | A | 11/1999 | Assmus et al. | 7,112,713 B2 | 9/2006 | Sceusa |
| 5,997,886 | A | 12/1999 | Peffly et al. | 7,122,199 B2 | 10/2006 | Sagel et al. |
| 6,004,566 | A | 12/1999 | Freidman et al. | 7,138,458 B2 | 11/2006 | Cleary et al. |
| 6,004,578 | A | 12/1999 | Lee et al. | 7,217,853 B2 | 5/2007 | Kulichikhin et al. |
| 6,007,837 | A | 12/1999 | Enscore et al. | 7,323,161 B2 | 1/2008 | Choi et al. |
| 6,024,976 | A | 2/2000 | Miranda et al. | 7,384,650 B2 | 6/2008 | Chien |
| 6,045,811 | A | 4/2000 | Dirksing et al. | 7,456,331 B2 | 11/2008 | Kulichikhin et al. |
| 6,051,609 | A | 4/2000 | Yu et al. | 7,744,918 B2 | 6/2010 | Yamaguchi et al. |
| 6,063,399 | A | 5/2000 | Assmus et al. | 2001/0006677 A1 | 7/2001 | Mcginity et al. |
| 6,068,650 | A | 5/2000 | Hofmann et al. | 2001/0021374 A1 | 9/2001 | Montgomery |
| 6,072,100 | A | 6/2000 | Mooney et al. | 2001/0046471 A1 | 11/2001 | Marek et al. |
| 6,075,626 | A | 6/2000 | Mizutani et al. | 2002/0004190 A1 | 1/2002 | Diasti et al. |
| 6,083,421 | A | 7/2000 | Huang et al. | 2002/0009420 A1 | 1/2002 | McLaughlin |
| 6,093,328 | A | 7/2000 | Santina | 2002/0048602 A1 | 4/2002 | Flore et al. |
| 6,096,328 | A | 8/2000 | Sagel et al. | 2002/0076487 A1 | 6/2002 | Zajac |
| 6,135,126 | A | 10/2000 | Joshi | 2002/0106335 A1 | 8/2002 | Orlowski et al. |
| 6,142,939 | A | 11/2000 | Eppstein et al. | 2002/0131990 A1 | 9/2002 | Barkalow et al. |
| 6,146,654 | A | 11/2000 | Kubo | 2002/0197284 A1 | 12/2002 | Luo et al. |
| 6,153,215 | A | 11/2000 | Samuelsen et al. | 2003/0035841 A1 | 2/2003 | Dzija |
| 6,162,456 | A | 12/2000 | Dunbar et al. | 2003/0055190 A1 | 3/2003 | Parker et al. |
| 6,165,499 | A | 12/2000 | Kleinsorgen et al. | 2003/0068376 A1 | 4/2003 | Chen et al. |
| 6,177,096 | B1 | 1/2001 | Zerbe et al. | 2003/0100654 A1 | 5/2003 | Cheang et al. |
| 6,193,993 | B1 | 2/2001 | Musashi et al. | 2003/0103427 A1 | 6/2003 | Yeo et al. |
| 6,197,331 | B1 | 3/2001 | Lerner et al. | 2003/0152528 A1 | 8/2003 | Singh et al. |
| 6,201,164 | B1 | 3/2001 | Wulff et al. | 2003/0152615 A1 | 8/2003 | Houze et al. |
| 6,212,671 | B1 | 4/2001 | Kanehira et al. | 2003/0170308 A1 | 9/2003 | Cleary et al. |
| 6,221,341 | B1 | 4/2001 | Montgomery | 2003/0180229 A1 | 9/2003 | Kosti |
| 6,221,383 | B1 | 4/2001 | Miranda et al. | 2003/0225356 A1 | 12/2003 | Kulichikhin et al. |
| 6,231,885 | B1 | 5/2001 | Carrara | 2003/0235549 A1 | 12/2003 | Singh et al. |
| 6,248,363 | B1 | 6/2001 | Patel et al. | 2004/0005277 A1 | 1/2004 | Willison et al. |
| 6,264,981 | B1 | 7/2001 | Zhang et al. | 2004/0053901 A1 | 3/2004 | Chien |
| 6,270,792 | B1 * | 8/2001 | Guillemet et al. ............ 424/443 | 2004/0105834 A1 | 6/2004 | Singh et al. |
| 6,275,728 | B1 | 8/2001 | Venkatraman et al. | 2004/0136927 A1 | 7/2004 | Kim et al. |
| 6,306,370 | B1 | 10/2001 | Jensen et al. | 2004/0166147 A1 | 8/2004 | Lundy et al. |
| 6,312,666 | B1 | 11/2001 | Oxman et al. | 2004/0219111 A1 | 11/2004 | Kim et al. |
| 6,312,670 | B1 | 11/2001 | Montgomery | 2004/0258723 A1 | 12/2004 | Singh et al. |
| 6,316,022 | B1 | 11/2001 | Mantelle et al. | 2005/0031554 A1 | 2/2005 | Kim et al. |
| 6,322,774 | B1 | 11/2001 | Jensen et al. | 2005/0113510 A1 | 5/2005 | Feldstein et al. |
| 6,329,472 | B1 | 12/2001 | Kim et al. | 2005/0208110 A1 | 9/2005 | Singh et al. |
| 6,368,576 | B1 | 4/2002 | Jensen et al. | 2005/0215727 A1 | 9/2005 | Feldstein et al. |
| 6,419,905 | B1 | 7/2002 | Alvarez Hernandez | 2005/0228113 A1 | 10/2005 | Baumer et al. |
| 6,419,906 | B1 | 7/2002 | Xu et al. | 2005/0256223 A1 | 11/2005 | Kolb et al. |
| 6,451,240 | B1 | 9/2002 | Sherman et al. | 2006/0034905 A1 | 2/2006 | Singh et al. |
| 6,451,777 | B1 | 9/2002 | Bradbury et al. | 2006/0110434 A1 | 5/2006 | Yamaguchi et al. |
| 6,461,636 | B1 | 10/2002 | Arth et al. | 2006/0168905 A1 | 8/2006 | Blanc et al. |
| 6,488,913 | B2 | 12/2002 | Orlowski et al. | 2006/0171906 A1 | 8/2006 | Singh et al. |
| 6,517,350 | B2 | 2/2003 | Diasti et al. | 2006/0182788 A1 | 8/2006 | Singh et al. |
| 6,552,147 | B2 | 4/2003 | Parker et al. | 2006/0193793 A1 | 8/2006 | Kim et al. |
| 6,558,654 | B2 | 5/2003 | McLaughlin | 2006/0193794 A1 | 8/2006 | Kim et al. |
| 6,562,363 | B1 | 5/2003 | Mantelle et al. | 2008/0161492 A1 | 7/2008 | Cleary et al. |
| 6,576,712 | B2 | 6/2003 | Feldstein et al. | 2009/0258060 A1 | 10/2009 | Cleary et al. |
| 6,585,997 | B2 | 7/2003 | Moro et al. | | | |
| 6,591,124 | B2 | 7/2003 | Sherman et al. | FOREIGN PATENT DOCUMENTS | | |
| 6,596,298 | B2 | 7/2003 | Leung et al. | CA | 2451431 | 1/2003 |
| 6,602,912 | B2 | 8/2003 | Hsu et al. | CA | 2506073 | 6/2004 |
| 6,611,706 | B2 | 8/2003 | Avrahami et al. | DE | 8509793 | 5/1985 |
| 6,638,528 | B1 | 10/2003 | Kanios | DE | 4219368 | 6/1992 |
| 6,656,493 | B2 | 12/2003 | Dzija | EP | 0184470 | 6/1986 |
| 6,667,410 | B2 | 12/2003 | Manbus et al. | EP | 0303445 | 2/1989 |
| 6,673,363 | B2 | 1/2004 | Luo et al. | EP | 0364211 | 4/1990 |
| 6,682,721 | B2 | 1/2004 | Kim et al. | EP | 0371421 | 6/1990 |
| 6,689,344 | B2 | 2/2004 | Chang et al. | EP | 0511782 | 11/1992 |
| 6,696,459 | B1 | 2/2004 | Jones et al. | EP | 0516026 | 12/1992 |
| 6,708,060 | B1 | 3/2004 | Avrahami et al. | EP | 0545594 | 6/1993 |
| 6,709,671 | B2 | 3/2004 | Zerbe et al. | EP | 0581581 | 2/1994 |
| 6,711,435 | B2 | 3/2004 | Avrahami | EP | 0672094 | 9/1995 |
| 6,714,497 | B2 | 3/2004 | Yeo et al. | EP | 0737477 | 10/1996 |
| 6,750,291 | B2 | 6/2004 | Kim et al. | EP | 0838225 | 4/1998 |
| 6,759,030 | B2 | 7/2004 | Kosti | EP | 0848960 | 6/1998 |
| 6,762,202 | B2 | 7/2004 | Marek et al. | EP | 1066823 | 1/2001 |
| 6,780,401 | B2 | 8/2004 | Kim et al. | GB | 1108837 | 4/1968 |
| 6,783,769 | B1 | 8/2004 | Arth et al. | JP | 58-162681 | 9/1983 |
| 6,803,420 | B2 | 10/2004 | Cleary et al. | JP | 59-196817 | 11/1984 |

| | | |
|---|---|---|
| JP | 01-151524 A | 6/1989 |
| JP | 03-066612 | 3/1991 |
| JP | 03-247334 | 5/1991 |
| JP | 03-275619 | 6/1991 |
| JP | 04-266818 | 9/1992 |
| JP | 06-100467 | 4/1994 |
| JP | 10-017448 | 1/1998 |
| JP | 2001-213768 A | 7/2001 |
| JP | 2002-029949 | 1/2002 |
| JP | 2002-145746 A | 5/2002 |
| KR | 20020045224 | 6/2002 |
| KR | 20030000299 | 1/2003 |
| KR | 20030000528 | 1/2003 |
| KR | 20030003969 | 1/2003 |
| KR | 20030003973 | 1/2003 |
| RU | 1459215 | 11/1995 |
| RU | 1459215 A1 | 11/1995 |
| WO | WO 89/03859 | 5/1989 |
| WO | WO 90/07940 A1 | 7/1990 |
| WO | WO 93/02717 | 2/1993 |
| WO | WO 94/05340 | 3/1994 |
| WO | WO 96/19205 | 6/1996 |
| WO | WO 97/11676 | 4/1997 |
| WO | WO 98/20862 A1 | 5/1998 |
| WO | WO 98/26763 A1 | 6/1998 |
| WO | WO 98/37870 | 9/1998 |
| WO | WO 98/55044 | 12/1998 |
| WO | WO 99/11728 A1 | 3/1999 |
| WO | WO 99/17738 | 4/1999 |
| WO | WO 99/44678 | 9/1999 |
| WO | WO 99/47128 | 9/1999 |
| WO | WO 99/54422 | 10/1999 |
| WO | WO 99/55312 A2 | 11/1999 |
| WO | WO 00/16725 | 3/2000 |
| WO | WO 00/18365 A2 | 4/2000 |
| WO | WO 00/61120 A1 | 10/2000 |
| WO | WO 00/69421 | 11/2000 |
| WO | WO 01/01958 A1 | 1/2001 |
| WO | WO 01/07018 A1 | 2/2001 |
| WO | WO 01/26637 | 4/2001 |
| WO | WO 01/68045 | 9/2001 |
| WO | WO 01/87276 | 11/2001 |
| WO | WO 02/00182 A3 | 1/2002 |
| WO | WO 02/04570 | 1/2002 |
| WO | WO 02/087642 | 11/2002 |
| WO | WO 02/087645 | 11/2002 |
| WO | WO 02/089849 | 11/2002 |
| WO | WO 03/000216 | 1/2003 |
| WO | WO 03/089046 | 10/2003 |
| WO | WO 03/099344 | 12/2003 |
| WO | WO 2004/045569 | 6/2004 |
| WO | WO 2004/054638 | 7/2004 |
| WO | WO 2004/071323 | 8/2004 |
| WO | WO 2004/093786 | 11/2004 |
| WO | WO 2004/103201 | 12/2004 |
| WO | WO 2005/027768 | 3/2005 |
| WO | WO 2006/017807 | 2/2006 |
| WO | WO 2006/029407 | 3/2006 |
| WO | WO 2006/069236 | 6/2006 |
| WO | WO 2006/074173 | 7/2006 |
| WO | WO 2006/081497 | 8/2006 |
| WO | WO 2006/124639 | 11/2006 |
| WO | WO 2007/119656 | 10/2007 |
| WO | WO 2010/083035 | 7/2010 |

OTHER PUBLICATIONS

U.S. Appl. No. 10/137,664, filed May 1, 2002, Cleary, et al.
U.S. Appl. No. 10/359,548, filed Feb. 5, 2003, Singh, et al.
U.S. Appl. No. 10/661,103, filed Sep. 12, 2003, Singh, et al.
U.S. Appl. No. 10/936,887, filed Sep. 8, 2004, Feldstein, et al.
U.S. Appl. No. 10/848,538, filed May 17, 2004, Singh, et al.
U.S. Appl. No. 11/028,702, filed Jan. 3, 2005, Feldstein, et al.
Aubin, et al., "Analysis of the glass transition temperature of miscible polymer blends", Macromolecules, vol. 21, pp. 2945-2949, (1988).
Bairamov, et al., "Kinetic parameters of poly(N-vinyl pyrrolidone) spontaneous mixing with short-chain poly(ethylene glycol)", Polym. Mater. Sci. Eng., vol. 82, pp. 7-8, (2000).
Borodulina, et al. "Viscoelasticity of Pressure-sensitive adhesive and bioadhesive hydrogels under compressive load", Proceed. 24th Annual Meeting Adhesion Soc., pp. 147-149, (2001).
Chalykh, et al., "Effects of composition and hydration on adhesive properties of poly(N-vinyl pyrrolidone)-poly(ethylene glycol) hydrogels", Polym. Mater. Sci. Eng., vol. 81, pp. 456-457, (1999).
Chalykh, et al., "Fracture mechanics of poly(N-vinyl pyrrolidone)-poly(ethylene glycol) hydrogel adhesive joints," Polym. Mater. Sci. Eng., vol. 81, pp. 427-428, (1999).
Chalykh, et al., "Pressure-sensitive adhesion in the blends of poly(N-vinyl pyrrolidone) and poly(ethylene glycol) of disparate chain lengths," J. Adhesion, vol. 78, pp. 667-694, (2002).
Cleary, et. al., A new polymer blend adhesive with combined properties to adhere to either skin or mucosa for drug delivery, podium abstract, 30th Annual Meeting and Exposition of the Controlled Release Society, Glasgow, Scotland, Jul. 19-23, 2003, Abstract #123.
Database WPI Section Ch, Week 198451, Derwent Publications Ltd., London, GB; Class A96, AN 1984-315114 & JP 59196817 A (Sekisuki Chem Ind Co Ltd) Nov. 8, 1984 abstract.
Database WPI Section Ch, Week 199150, Derwent Publications Ltd., London, GB; Class A18, AN 1991-366353 & JP 03247334 A (Sumitomo Rubber Ind Ltd) Nov. 5, 1991 abstract.
Database WPI Section Ch, Week 199118, Derwent Publications Ltd., London, GB; Class A96, AN 1991-128478 & JP 03066612 A (Sato Pharm Co Ltd) Mar. 22, 1991 abstract.
Database WPI Section Ch, Week 199627, Derwent Publications Ltd., London, GB; Class A14, An 1996-266746 & SU 1459215 A (A Med Cardiology Res Centre) Nov. 20, 1995 abstract.
Feldstein, et al., "A structure-property relationship and quantitative approach to the development of universal transdermal drug delivery system," NBC Risks, vol. 25, pp. 441-458, (1999).
Feldstein, et al., "Coherence of thermal transitions in poly(N-vinyl pyrrolidone)-poly(ethylene glycol) compatible blends: 1. Interrelations among the temperatures of melting, maximum cold crystallization rate and glass transition", Polymer, vol. 41, pp. 5327-5338, (2000).
Feldstein, et al., "Coherence of thermal transitions in poly(N-vinyl pyrrolidone)-poly(ethylene glycol) compatible blends: 2. The temperature of maximum cold crystallization rate versus glass transition", Polymer, vol. 41, pp. 5339-5348, (2000).
Feldstein, et al., "Coherence of thermal transitions in poly(N-vinyl pyrrolidone)-poly(ethylene glycol) compatible blends: 3. Impact of sorbed water upon phase behavior", Polymer, vol. 41, pp. 5349-5359, (2000).
Feldstein, et al., "Correlations between activation energy for debonding and that for self-diffusion in pressure-sensitive hydrogels", Proceed. 24th Annual Meeting Adhesion Soc., pp. 137-140, (2001).
Feldstein, et al., "Contribution of molecular mobility to debonding of pressure-sensitive adhesive hydrogels", Polym. Mater. Sci. Eng., vol. 81, pp. 467-468, (1999).
Feldstein, et al., "Effect of hydrophilic matrix hydration on transdermal drug delivery kinetics: I. The matrix hydration In Vivo and In Vitro", Prediction of Percutaneous Penetration, vol. 4b, pp. 61-64, Brian, et al., (Eds.) (1996).
Feldstein, et al., "Effect of hydrophilic matrix hydration on transdermal drug delivery kinetics: II. In Vitro cytosine Delivery From Cypercuten TTS", Prediction of Percutaneous Penetration, vol. 4b, pp. 65-67, Brian, et al., (Eds.) (1996).
Feldstein, et al., "Effect of hydrophilic matrix hydration on transdermal drug delivery kinetics: III. In Vitro clonide delivery from clopercuten TTS", Prediction of Percutaneous Penetration, vol. 4b, pp. 68-70, Brian, et al., (Eds.) (1996).
Feldstein, et al., "Effect of hydrophilic matrix hydration on transdermal drug delivery kinetics: IV. In Vitro-In Vivo correlation," Prediction of Percutaneous Penetration, vol. 4b, pp. 71-73, Brian, et al., (eds.) (1996).
Feldstein, et al., "Effects of chains orientation, free volume and interaction on glass transition in poly(N-vinyl pyrrolidone)-poly(ethylene glycol) blends involving a stoichiometric hydrogen-bonded network complex", Polym. Mater. Sci. Eng., vol. 82, pp. 365-366, (2000).

Feldstein, et al., "General approach to the molecular design of hydrophilic pressure-sensitive adhesives," Proc. 25th Ann. Mtg. and 2nd World Congress on Adhesion and Related Phenomena, Orlando, FL, vol. 1, pp. 292-294 (2002).

Feldstein, et al., "Molecular insight into rheological and diffusion determinants of pressure sensitive adhesion", Proceed. 23rd Annual Meeting Adhesion Soc., pp. 54-56, (2000).

Feldstein, et al., "Peculiarities of glass transition temperature relation to the composition of poly(N-vinyl pyrrolidone) blends with short chain poly(ethylene glycol)", Polymer, vol. 42, pp. 7719-7726, (2001).

Feldstein, et al., "Quantitative relationship between molecular structure and adhesion of PVP-PEG hydrogels", Polym. Mater. Sci Eng., vol. 81, pp. 465-466, (1999).

Feldstein, et al., "Relation of glass transition temperature to the hydrogen bonding degree and energy in poly(N-vinyl pyrrolidone) blends with hydroxyl-containing plasticizers: 2. Effects of poly(ethylene glycol) chain length", Polymer, vol. 42, pp. 981-990, (2001).

Feldstein, et al., "Universal hydrophilic drug-containing adhesive matrix for systemic and topical transdermal drug delivery", Proc. 1st World Meeting APGI/APV, Budapest, 9/11, 2 pages, (1995).

Handbook of Pharmaceutical Excipients, Arther H. Kibbe, ed., 3rd ed., pp. 401-406, (2000).

Hawley's Condensed Chemical Dictionary, 14th Edition, Citation, "Oligomer, A polymer molecule of only a few monomer units (dimer, trimer tetramer)", John Wiley and Sons, Inc., (2002).

International Search Report for PCT/US2000/18557 mailed Oct. 17, 2000.

International Search Report for PCT/US2001/21417 mailed Feb. 25, 2002.

International Search Report for PCT/US2002/13680 mailed Sep. 18, 2002.

International Search Report for PCT/US2002/14260 Mailed Sep. 17, 2002.

International Search Report for PCT/US2002/14725 mailed Sep. 27, 2002.

International Search Report for PCT/US2003/16408 Mailed Dec. 8, 2003.

International Search Report for PCT/US2003/039717 Mailed Jun. 28, 2004.

International Search Report for PCT/US2004/003443 Mailed Aug. 20, 2004.

International Search Report for PCT/US2004/011567 Mailed Jan. 10, 2006.

International Search Report for PCT/US2004/015448 Mailed Dec. 28, 2004.

International Search Report for PCT/US2004/029620 Mailed Jun. 1, 2005.

International Search Report for PCT/US2005/0002873 Mailed Apr. 27, 2005.

International Search Report for PCT/US2005/0034439 Mailed Jul. 19, 2006.

International Search Report for PCT/US2005/0046577 Mailed Jul. 26, 2006.

International Search Report for PCT/US/2005/028063 Mailed Apr. 28, 2006.

International Search Report for PCT/US/2005/032525 Mailed Mar. 17, 2006.

International Search Report for PCT/US/2006/000098 Mailed Nov. 3, 2006.

International Search Report for PCT/US2006/0003091 Mailed Oct. 11, 2006.

International Search Report for PCT/US2006/018500 Mailed Sep. 21, 2006.

Kotomin, et al., "Squeeze-recoil analysis of adhesive hydrogels and elastomers", Polym. Mater. Sci. Eng., vol. 81, pp. 425-426, (1999).

Kotomin, et al., "Durability and fracture of some visceolastic adhesives," Proceed. of the 23rd Annual Meeting of the Adhesion Soc., pp. 413-415, (2000).

MSDS (Material Safety Data Sheet), Lactic Acid, No. L0522, (2008).

Patent Abstracts of Japan, vol. 017, No. 055 (C-I023) Feb. 3, 1993 & JP 04 266818 A (Sekisui Chem Co Ltd), Sep. 22, 1992 abstract.

Roos, et al., "Probe tack investigation of poly(vinyl pyrrolidone)-poly(ethylene glycol) blends", Proceed. 24th Annual Meeting Adhesion Soc., pp. 277-279, (2001).

Sintov, et al., "Radiofrequency-driven skin microchanneling as a new way for electrically assisted transdermal delivery of hydrophilic drugs", J. Contr.Release, vol. 89, pp. 311-320, (2003).

Supplementary European Search Report for EP04783729.9 Mailed Jun. 5, 2009.

Vartapian, et al., "Self-diffusion in poly(N-vinyl pyrrolidone)-polyethylene glycol) systems", Colloid Polym. Sci., vol. 279, pp. 532-538, (2001).

Vartapian, et al., "Molecular dynamics in poly(N-vinyl pyrrolidone)-polyethylene glycol) blends by pulsed-field gradient NMR method: effects of aging, hydration and PEG chain length", Macromol. Chem. Phys., vol. 202, pp. 2648-2652, (2001).

Schehlmann, "Polyvinylcaprolactam: physical and cosmetic properties of a new hair fixative resin", Lecture, held at the IN-COSMET-ICS, Dusseldorf, 6 pages (1997).

U.S. Appl. No. 11/150,811, filed Jun. 10, 2005, Feldstein, et al.

U.S. Appl. No. 12/687,586, filed Jan. 11, 2009, Singh, et al.

Emla Cream, (lidocaine 2.5% and prilocaine 2.5%), EMLA Anesthetic Disc, (lidocaine 2.5% and prilocaine 2.5% cream), "Topical anesthetic for dermal analgesia", AstraZeneca Product Monograph, 46 pgs. Revised May 25, 2010.

EUDRAGIT® RL 100, "EUDRAGIT® RL 100 is a copolymer of ethyl acrylate, methyl methacrylate and a low content of methacrylic acid ester with quaternary ammonium groups. The ammonium groups are present as salts and make the polymers permeable", Product Information, Accessed online from: http://eudragit.evonik.com/product/eudragit/en/products-services/eudragit-products/sustained-release-formulations/rl-100/pages/default.aspx, 1 page, accessed on Apr. 15, 2011.

EUDRAGIT® RS 100, "EUDRAGIT® RS 100 is a copolymer of ethyl acrylate, methyl methacrylate and a low content of methacrylic acid ester with quaternary ammonium groups. The ammonium groups are present as salts and make the polymers permeable", Product Information, Accessed online from: http://eudragit.evonik.com/product/eudragit/en/products-services/eudragit-products/sustained-release-formulations/rs-100/pages/default.aspx, 1 page, accessed on Apr. 15, 2011.

Evonic Industries, "EUDRAGIT® E 100: EUDRAGIT®E 100 is a cationic copolymer based on dimethylaminoethyl methacrylate, butyl methacrylate, and methyl methacrylate", Product Information, Accessed Online from http://eudragit.evonik.com, 1 page (2011).

Evonic Industries, "EUDRAGIT® L 12,5 and EUDRAGIT® S 12,5", Product Information, Accessed Online from http://eudragit.evonik.com, 1 page (2011).

Evonic Industries, "EUDRAGIT® L 12,5 and EUDRAGIT® RS 12,5", Product Information, Accessed Online from http://eudragit.evonik.com, 1 page (2011).

Evonic Industries, "EUDRAGIT® NE 30 D: EUDRAGIT® NE 30 D is the aqueous dispersion of a neutral copolymer based on ethyl acrylate and methyl methacrylate", Product Information, Accessed Online from http://eudragit.evonik.com, 1 page (2011).

Whelan Polymer Technology Dictionary, Citation *Butyl Rubber*, Chapman Hall, 2-6 Boundry Row, London, UK, vol. 1, pp. 53 (1994).

"Aquasorb® A-500 Cellulose Gum (CMC)", Hercules Incorporated, Aqualon Division, Product Data No. 4234, 2 pgs. (2005).

* cited by examiner

HYDROGEL COMPOSITIONS

CROSS-REFERENCE TO RELATED APPLICATIONS

This application is a divisional of U.S. patent application Ser. No. 10/137,664, filed May 1, 2002, which claims priority under 35 U.S.C. §119(e)(1) to provisional U.S. Patent Application Ser. No. 60/288,008, filed May 1, 2001.

TECHNICAL FIELD

This invention relates generally to hydrogel compositions, and more particularly relates to a novel hydrogel composition useful in a variety of contexts involving application of a wound dressing, cushion, or the like to an individual's skin or other body surface. The assignees of this application, Corium International, Inc. and the A.V. Topchiev Institute of Petrochemical Synthesis, Russian Academy of Sciences, are parties to a joint research agreement covering work in this and other fields.

BACKGROUND

Various types of bandages and wound dressings are known and used to protect wounds and burns. Typically, wound dressings are fabricated with an absorbent material so that wound exudate is removed and the wound dried, facilitating healing. Wound dressings may also contain one or more pharmacologically active agents such as antibiotics, local anesthetics, or the like. Commonly used wound dressings include fibrous materials such as gauze and cotton pads, which are advantageous in that they are absorbent but problematic in that fibers may adhere to the wound or newly forming tissue, causing wound injury upon removal. Other wound dressings have been prepared with foams and sponges, but the absorbance of these materials is often limited. Furthermore, such wound dressings require the use of adhesive tape, as they are not themselves adhesive.

To improve the absorbance of conventional fibrous wound dressings, water-swellable polymers, or "hydrogels," have been incorporated into gauze or other fibrous materials for application to a wound. For example, U.S. Pat. No. 5,527,271 to Shah et al. describes a composite material made from a fibrous material, such as cotton gauze, impregnated with a thermoplastic hydrogel-forming copolymer containing both hydrophilic and hydrophobic segments. While the wound dressings are described as having increased absorptive capacity, the adhesion of fibers to the wound or newly forming tissue remains a significant disadvantage.

Another approach has been to use water-swellable polymeric materials instead of gauze, cotton, and the like. Wound-contacting surfaces made of such materials are not only more absorbent than conventional fibrous materials, they are also advantageous in that there is no risk of fiber adhesion during wound healing and upon removal of the wound dressing. Such wound dressings are disclosed, for example, in U.S. Pat. No. 4,867,748 to Samuelsen, which describes the use of an absorbent wound-contacting composition made from a water-soluble or water-swellable hydrocolloid blended with or dispersed in a water-insoluble, viscous, elastomeric binder. U.S. Pat. No. 4,231,369 to Sørensen et al. describes "hydrocolloid plasters" as sealing materials for ostomy devices, the materials consisting of a continuous hydrophobic phase made from a hydrophobic pressure-sensitive adhesive, a plasticizer, and a tackifying resin, with a discontinuous phase dispersed therein consisting of a water-soluble or water-swellable polymer. Such plasters are also described in U.S. Pat. No. 5,643,187 to Naestoft et al. U.S. Pat. No. 6,201,164 to Wulff et al. describes a somewhat different type of hydrocolloid wound gel, consisting of a water-insoluble, water-swellable, crosslinked cellulose derivative, an alginate, and water.

Hydrogel bandages have also been employed in wound dressings, as described, for example, in U.S. Pat. No. 4,093,673 to Chang et al. Hydrogel bandages are made from a liquid absorbing crosslinked polymer and have a high water content prior to use. The high water content causes the hydrogel to exhibit very little or no adhesion, requiring the use of adhesive tape or a plaster such as $2^{nd}$ Skin® dressing available from Spenco Medical Ltd., U.K.

Numerous problems continue to be encountered with gel-based wound dressings made with hydrocolloids and hydrogels, however. The reason for this is, in part, that there are conflicting requirements for an ideal material. The material should not be so adhesive that it tends to adhere to a wound and thus cause pain or further injury upon removal. However, a wound dressing should adhere sufficiently to a body surface so that adhesive tapes and adhesive plasters are not necessary. Peripheral adhesives can be used, but require an additional manufacturing consideration. In addition, a wound dressing should conform to the contours of the skin or other body surface, both during motion and at rest. For wound dressings that also serve as a ushioning pad, higher cohesive strength hydrogels should be used, without any loss in adhesion. Ideal hydrogel adhesives also display very high swelling upon contact with water, exhibit little or no cold flow during use, and can be easily tailored during manufacture to optimize properties such as adhesive strength, cohesive strength, and hydrophilicity. It would also be desirable to be able to manufacture adhesive hydrogels using a simple extrusion process, obviating the need for organic solvents and the conventional, time-consuming blending and casting method.

Another desired goal, with respect to wound dressings, would enable an adhesive hydrogel to be prepared that meets all of the foregoing criteria and is, in addition, translucent. To date, the hydrogel materials used in wound dressings have been opaque. With a translucent material, it becomes possible to view the degree of wound healing through the dressing, in turn meaning that the dressing does not need to be removed, changed, or partially peeled back from the skin in order to assess the degree of healing.

It would also be ideal if a hydrogel adhesive met all of the above criteria and could also be adapted for uses other than wound healing. Such uses might include, by way of example, fabrication of transdermal drug delivery devices, preparation of medicated gels for topical and transdermal pharmaceutical formulations, use in pressure-relieving cushions (which may or may not be medicated), use as sealants for ostomy devices and prostheses, use as conductive adhesives for attachment of electroconductive articles such as electrodes to the skin, and the like.

SUMMARY OF THE INVENTION

It is a primary object of the invention to provide adhesive hydrogel-containing compositions that meet all of the above-discussed needs in the art.

In a first embodiment, the invention pertains to a hydrogel-containing composition comprised of a discontinuous hydrophobic phase and a hydrophilic phase that is either continuous or discontinuous. The discontinuous hydrophobic phase includes at least the following components: a hydrophobic polymer, typically a hydrophobic pressure-sensitive adhesive (PSA) polymer; a plasticizer, preferably a plasticizing elastomer, typically a styrene-based copolymer; a low molecular weight tackifying resin; and, optionally, up to about 2 wt. % of an antioxidant. Generally, although not necessarily, the hydrophobic polymer and the tackifying resin each represent approximately 5 wt. % to 15 wt. % of the composition, while the plasticizer represents approximately 25 wt. % to 45 wt. % of the composition.

For those compositions in which the hydrophilic phase is discontinuous, the hydrophilic phase is composed of a crosslinked hydrophilic polymer that is insoluble in water under standard conditions of storage and use. A preferred polymer is a crosslinked cellulosic polymer such as crosslinked sodium carboxymethylcellulose. In this case, as may be deduced from the above, the crosslinked hydrophilic polymer represents approximately 25 wt. % to 65 wt. % of the overall composition.

For those compositions in which the hydrophilic phase is continuous, several components are combined to form the hydrophilic phase: a water-swellable, water-insoluble polymer, i.e., a polymer that is capable of swelling when immersed in an aqueous liquid but that is insoluble in water within a selected pH range (generally up to a pH of at least 7.5-8.5), preferably an acrylic acid or acrylic acid ester polymer or copolymer (an "acrylate" polymer) or a cellulose ester; a low molecular weight plasticizer such as low molecular weight polyethylene glycol (e.g., polyethylene glycol 400), dioctyl adipate or diethyl phthalate; and a blend of a relatively high molecular weight hydrophilic polymer and a lower molecular weight complementary oligomer that is capable of crosslinking the hydrophilic polymer through hydrogen bonds. In this case, i.e., with a continuous hydrophilic phase, the water-swellable, water-insoluble polymer represents approximately 2 wt. % to 15 wt. % of the hydrogel composition, the low molecular weight plasticizer represents approximately 2.5 wt. % to 5.0 wt. % of the hydrogel composition, and the hydrophilic polymer/complementary oligomer blend represents approximately 17.5 wt. % to 45 wt. % of the hydrogel composition. In some cases, however, the same molecular entity can serve as both the low molecular weight plasticizer and the complementary oligomer.

In another embodiment, the hydrogel composition is entirely composed of a continuous hydrophilic phase comprising a water-swellable, water-insoluble polymer as described above, preferably an acrylate polymer or a cellulose ester; optionally, a low molecular weight plasticizer; and a blend of a relatively high molecular weight hydrophilic polymer and a lower molecular weight complementary oligomer (also as above). In this embodiment, the water-swellable, water-insoluble polymer is selected so as to provide the desired adhesion profile with respect to hydration. That is, when the water-swellable, water-insoluble polymer is a cellulose ester, the hydrogel composition is generally tacky prior to contact with water (e.g., with a moist surface) but gradually loses tack as the composition absorbs moisture. When the water-swellable, water-insoluble polymer is an acrylate polymer or copolymer, a hydrogel composition is provided that is generally substantially nontacky prior to contact with water, but become tacky upon contact with a moist surface. Acrylate-containing systems also provide for a hydrogel composition that can be reversibly dried; that is, following removal of water and any other solvents that may be present, the dried hydrogel may be reconstituted to its original state by addition of water.

In either of these embodiments, the hydrogel composition may also include conventional additives such as fillers, preservatives, pH regulators, softeners, thickeners, pigments, dyes, refractive particles, stabilizers, toughening agents, pharmaceutical agents, and permeation enhancers. These additives, and amounts thereof, are selected in such a way that they do not significantly interfere with the desired chemical and physical properties of the hydrogel composition.

The properties of the hydrogel composition are readily controlled by adjusting one or more parameters during fabrication. For example, the adhesive strength of the hydrogel composition can be controlled during manufacture in order to increase, decrease, or eliminate adhesion. This can be accomplished by varying type and/or amount of different components, or by changing the mode of manufacture. For example, incorporating greater amounts of the plasticizer and the tackifying resin in the discontinuous hydrophobic phase will increase tack, while reducing the amounts of those components or incorporating detackifier additives will decrease tack. Also, with respect to the fabrication process, compositions prepared using a conventional melt extrusion process are generally, although not necessarily, somewhat less tacky than compositions prepared using a solution cast technique. In addition, certain hydrogel compositions, particularly those containing or entirely composed of a continuous hydrophilic phase, may be rendered translucent by changing the relative quantities of the components in the hydrophilic phase (e.g., by decreasing the amount of the cellulose ester), or by changing the fabrication method (translucent hydrogels are more readily obtained using solution casting than melt extrusion). Furthermore, the degree to which the hydrogel composition will swell upon contact with water can be varied by selecting different water-swellable polymers, and, in those compositions containing a continuous hydrophilic phase, by adjusting the ratio of the water-swellable, water-insoluble polymer to the hydrophilic polymer/complementary plasticizer blend.

In another embodiment, a drug delivery system is provided comprising an active agent in a hydrogel composition as described above, wherein the system has a body-contacting surface and an outer surface, with the hydrogel composition present within a region of the body-contacting surface. The body-contacting surface may be entirely comprised of the hydrogel composition, although it is preferred that the hydrogel composition be present in a central region on the body-contacting surface, with the perimeter of the body-contacting surface composed of a different skin contact adhesive. The drug delivery system may be designed for systemic delivery of an active agent, e.g., via the transdermal or transmucosal routes. The system may also be designed for topical administration of a locally active agent.

In a related embodiment, a wound dressing is provided comprised of a substrate for application to the wound region, wherein the substrate has a body-contacting surface and an outer surface, with the hydrogel composition present in a wound-contacting region of the body-contacting surface. As with the hydrogel-containing drug delivery systems, the body-contacting surface may be entirely comprised of the hydrogel composition, although it is preferred that the hydrogel composition be present in a central region on the body-contacting surface, with the perimeter of the body-contacting surface composed of a different skin contact adhesive. In this embodiment, the hydrogel is generally at least somewhat tacky upon application, but upon absorption of water present in the wound exudate, loses tack. Accordingly, in these compositions, incorporation of a cellulose ester is preferred.

The hydrogel compositions herein are also useful in a host of additional applications, e.g., in various types of pharmaceutical formulations, pressure-relieving cushions (which may or may not be medicated), bandages, ostomy devices, prosthesis securing means, face masks, sound, vibration or impact absorbing materials, and the like. Also, the hydrogel compositions may be rendered electrically conductive by incorporation of an electrically conductive material, and may thus be used for attaching an electroconductive article, such as an electrode (e.g., a transcutaneous electric nerve stimulation, or "TENS" electrode, an electrosurgical return electrode, or an EKG monitoring electrode), to an individual's body surface.

The adhesive hydrogel compositions of the invention provide a number of significant advantages relative to the prior art. In particular, the present hydrogel compositions:
 (1) may be fabricated so as to be translucent, which enables one to view the extent of wound healing without removing the hydrogel composition from the body surface;
 (2) display very high swelling upon contact with water;
 (3) exhibit little or no cold flow during use;
 (4) can be formulated so as to be reversibly dried, i.e., capable of reconstitution with water after drying, to provide the hydrogel in its original, hydrated state;
 (5) can be formulated so that tack increases or decreases in the presence of moisture;
 (6) are useful and versatile bioadhesives in a number of contexts, including wound dressings, active agent delivery systems for application to a body surface, pressure-relieving cushions, and the like; and
 (7) are readily modified during manufacture so that properties such as adhesion, absorption, translucence, and swelling can be optimized.

DETAILED DESCRIPTION OF THE INVENTION

I. Definitions and Nomenclature

Figure 1:
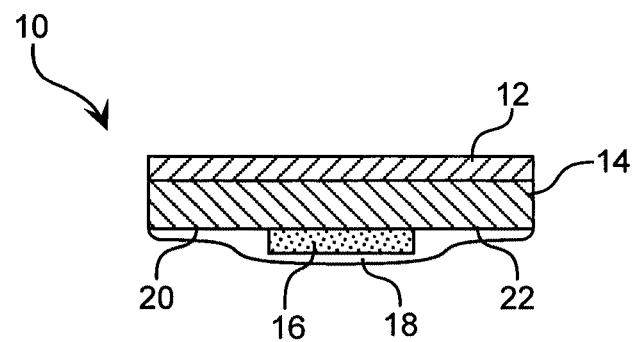
FIG. 1 schematically illustrates one embodiment of a wound dressing prepared with a hydrogel composition of the invention, wherein the dressing is composed of an outwardly facing backing layer and a body-facing skin contact adhesive layer laminated thereto, wherein a hydrogel composition of the invention is present as a film on an interior region of the body-contacting surface of the skin contact adhesive layer.

Before describing the present invention in detail, it is to be understood that unless otherwise indicated this invention is not limited to specific hydrogel materials or manufacturing processes, as such may vary. It is also to be understood that the terminology used herein is for the purpose of describing particular embodiments only, and is not intended to be limiting. It must be noted that, as used in this specification and the appended claims, the singular forms "a," "an," and "the" include plural referents unless the context clearly dictates otherwise. Thus, for example, reference to "a hydrophilic polymer" includes not only a single hydrophilic polymer but also a combination or mixture of two or more different hydrophilic polymers, reference to "a plasticizer" includes a combination or mixture of two or more different plasticizers as well as a single plasticizer, and reference to "a hydrophobic pressure-sensitive adhesive" includes a mixture of two or more such adhesives as well as a single such adhesive, and the like.

In describing and claiming the present invention, the following terminology will be used in accordance with the definitions set out below.

The definitions of "hydrophobic" and "hydrophilic" polymers are based on the amount of water vapor absorbed by polymers at 100% relative humidity. According to this classification, hydrophobic polymers absorb only up to 1 wt. % water at 100% relative humidity ("rh"), while moderately hydrophilic polymers absorb 1-10% wt. % water, hydrophilic polymers are capable of absorbing more than 10 wt. % of water, and hygroscopic polymers absorb more than 20 wt. % of water. A "water-swellable" polymer is one that absorbs an amount of water greater than at least 50 wt. % of its own weight, upon immersion in an aqueous medium.

The term "crosslinked" herein refers to a composition containing intramolecular and/or intermolecular crosslinks, whether arising through covalent or noncovalent bonding. "Noncovalent" bonding includes both hydrogen bonding and electrostatic (ionic) bonding.

The term "polymer" includes linear and branched polymer structures, and also encompasses crosslinked polymers as well as copolymers (which may or may not be crosslinked), thus including block copolymers, alternating copolymers, random copolymers, and the like. Those compounds referred to herein as "oligomers" are polymers having a molecular weight below about 1000 Da, preferably below about 800 Da.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-linking.

The term "hydrogel composition" refers to a composition that either contains a hydrogel or is entirely composed of a hydrogel. As such, "hydrogel compositions" encompass not only hydrogels per se but also compositions that not only contain a hydrogel but also contain one or more non-hydrogel components or compositions, e.g., hydrocolloids, which contain a hydrophilic component (which may contain or be a hydrogel) distributed in a hydrophobic phase.

The terms "tack" and "tacky" are qualitative. However, the terms "substantially nontacky" "slightly tacky" and "tacky," as used herein, may be quantified using the values obtained in a PKI or TRBT tack determination method, as follows. By "substantially nontacky" is meant a hydrogel composition that has a tack value that is less than about 25 g·cm/sec, by "slightly tacky" is meant a hydrogel composition that has a tack value in the range of about 25 g·cm/sec to about 100 g·cm/sec, and by "tack" is meant a hydrogel composition that has a tack value of at least 100 g·cm/sec.

The term "water-insoluble" refers to a compound or composition whose solubility in water is less than 5 wt. %, preferably less than 3 wt. %, more preferably less than 1 wt. % (measured in water at 20° C.).

The term "translucent" is used herein to signify a material capable of transmitting light so that objects or images can be seen through the material. Translucent materials herein may or may not be "transparent," meaning that the material is optically clear. The term "translucent" indicates that a material is not "opaque," in which case objects and images cannot be seen through the material.

The term "active agent" is used herein to refer to a chemical material or compound suitable for administration to a human patient and that induces a desired beneficial effect, e.g., exhibits a desired pharmacological activity. The term includes, for example, agents that are therapeutically effective, prophylactically effective, and cosmetically (and cosmeceutically) effective. Also included are derivatives and analogs of those compounds or classes of compounds specifically mentioned which also induce the desired beneficial effect.

By "transdermal" drug delivery is meant administration of a drug to the skin surface of an individual so that the drug passes through the skin tissue and into the individual's blood stream. Unless otherwise indicated, the term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of an active agent to a body surface such as the skin or mucosa, as in, for example, topical drug administration in the prevention or treatment of various skin disorders, the application of cosmetics and cosmeceuticals (including moisturizers, masks, sunscreens, etc.), and the like. Topical administration, in contrast to transdermal administration, provides a local rather than a systemic effect.

The term "body surface" is used to refer to any surface located on the human body or within a body orifice. Thus, a "body surface" includes, by way of example, skin or mucosal tissue, including the interior surface of body cavities that have a mucosal lining. Unless otherwise indicated, the term "skin" as used herein should be interpreted as including mucosal tissue and vice versa.

Similarly, when the term "transdermal" is used herein, as in "transdermal drug administration" and "transdermal drug delivery systems," it is to be understood that unless explicitly indicated to the contrary, both "transmucosal" and "topical" administration and systems are intended as well.

II. Hydrogel Compositions with a Discontinuous Hydrophobic Phase and a Discontinuous Hydrophilic Phase In a first embodiment, a hydrogel composition is provided that is comprised of:
(a) a discontinuous hydrophobic phase comprising
(i) a hydrophobic polymer,
(ii) a plasticizer, preferably elastomeric,
(iii) a tackifying resin, and
(iv) an optional antioxidant; and
(b) a discontinuous hydrophilic phase comprised of a crosslinked hydrophilic polymer.

The various components are as follows:
A. The Discontinuous Hydrophobic Phase
1. The Hydrophobic Polymer The hydrophobic polymer is typically a hydrophobic pressure-sensitive adhesive polymer, preferably a thermosetting polymer. Preferred hydrophobic PSA polymers are crosslinked butyl rubbers, wherein a "butyl rubber," as well known in the art, is an isoprene-isobutylene copolymer typically having an isoprene content in the range of about 0.5 to 3 wt. %, or a vulcanized or modified version thereof, e.g., a halogenated (brominated or chlorinated) butyl rubber. In a particularly preferred embodiment, the hydrophobic PSA polymer is butyl rubber crosslinked with polyisobutylene. Other suitable hydrophobic polymers include, for example, natural rubber adhesives, vinyl ether polymers, polysiloxanes, polyisoprene, butadiene acrylonitrile rubber, polychloroprene, atactic polypropylene, and ethylene-propylene-diene terpolymers (also known as "EPDM" or "EPDM rubber") (available as Trilene® 65 and Trilene® 67 from Uniroyal Chemical Co., Middlebury, Conn.). Still other suitable hydrophobic PSAs will be known to those of ordinary skill in the art and/or are described in the pertinent texts and literature. See, for example, the *Handbook of Pressure-Sensitive Adhesive Technology*, 2nd Ed., Satas, Ed. (New York: Von Nostrand Reinhold, 1989). Particularly preferred hydrophobic polymers are the crosslinked butyl rubbers available in the Kalar® series from Elementis Specialties, Inc. (Hightstown, N.J.), with Kalar® 5200, Kalar® 5215, Kalar® 5246, and Kalar® 5275 most preferred.

For most applications, the crosslinked hydrophobic polymer should have a sufficiently high degree of crosslinking so that the composition does not exhibit cold flow following application to a surface, e.g. a body surface such as skin. As will be appreciated by those in the art, the degree of crosslinking correlates with Mooney viscosity, a measure of the resistance of a raw or unvulcanized rubber to deformation as measured in a Mooney viscometer. A higher Mooney viscosity indicates a higher degree of crosslinking. The Mooney viscosity of preferred hydrophobic PSAs for use herein should be at least 20 cps at 25° C., and will generally be in the range of about 25 cps to 80 cps, preferably about 30 cps to 75 cps, at 25° C. The Mooney viscosities of the preferred Kalar® series polymers herein are as follows: Kalar® 5200, 40-45 cps; Kalar® 5215, 47-57 cps; Kalar® 5246, 30-40 cps; and Kalar® 5275, 70-75 cps (all at 25° C.).

The molecular weight of the hydrophobic PSA is not critical, although the molecular weight will typically be less than about 100,000 Da. The amount of the polymer generally, although not necessarily, represents in the range of about 5 wt. % to 15 wt. %, preferably about 7.5 wt. % to 12 wt. %, most preferably about 7.5 wt. % to 10 wt. %, of the composition after drying.

2. The Plasticizer

The plasticizer component of the hydrophobic phase acts is preferably, although not necessarily, an elastomeric polymer that acts not only as a plasticizer but also as a diluent. By "plasticizing" is meant that the component tends to decrease the glass transition temperature of the hydrophobic polymer and/or reduce its melt viscosity. Suitable plasticizing elastomers are natural and synthetic elastomeric polymers, including, for example, AB, ABA, and "multiarmed" $(AB)_x$ block copolymers, where for example, A is a polymerized segment or "block" comprising aryl-substituted vinyl monomers, preferably styrene, α-methyl styrene, vinyl toluene, and the like, B is an elastomeric, conjugated polybutadiene or polyisoprene block, and x has a value of 3 or more. Preferred elastomers are butadiene-based and isoprene-based polymers, particularly styrene-butadiene-styrene (SBS), styrene-butadiene (SB), styrene-isoprene-styrene (SIS), and styrene-isoprene (SI) block copolymers, where "S" denotes a polymerized segment or "block" of styrene monomers, "B" denotes a polymerized segment or block of butadiene monomers, and "I" denotes a polymerized segment or block of isoprene monomers. Other suitable elastomers include radial block copolymers having a SEBS backbone (where "E" and "B" are, respectively, polymerized blocks of ethylene and butylene) and I and/or SI arms. Natural rubber (polyisoprene) and synthetic polyisoprene can also be used.

Commercially available elastomers useful in the practice of the present invention include linear SIS and/or SI block copolymers such as Quintac® 3433 and Quintac® 3421, available from Nippon Zeon Company, Ltd. (U.S. sales office—Louisville, Ky.); Vector® DPX 559, Vector® 4111 and Vector® 4113, available from Dexco, a partnership of Exxon Chemical Co. (Houston, Tex.) and Dow Chemical Co. (Midland Mich.); and Kraton® rubbers, such as Kraton 604x, Kraton D-1107, Kraton D-1117, and Kraton D-1113, available from Shell Chemical Co. (Houston, Tex.). Kraton D-1107 is a predominantly SIS elastomer containing about 15% by weight SI blocks. Kraton D-1320x is an example of a commercially available $(SI)_x I_y$ multiarmed block copolymer in which some of the arms are polyisoprene blocks. Commercially available butadiene-based elastomers include SBS and/or SB rubbers, such as Kraton D-1101, D-1102 and D-1118X, from Shell Chemical Co.; Solprene® 1205, an SB block copolymer available from Housemex, Inc. (Houston, Tex.); and Kraton TKG-101 (sometimes called "Tacky G"), a radial block copolymer having an SEBS backbone (E=ethylene block; B=butylene block) and I and/or SI arms.

Other plasticizers may also be used, including, without limitation, the following low molecular weight plasticizers: dialkyl phthalates, dicycloalkyl phthalates, diaryl phthalates and mixed alkyl-aryl phthalates as represented by dimethyl phthalate, diethyl phthalate, dipropyl phthalate, di(2-ethylhexyl)phthalate, di-isopropyl phthalate, diamyl phthalate and dicapryl phthalate; alkyl and aryl phosphates such as tributyl phosphate, trioctyl phosphate, tricresyl phosphate, and triphenyl phosphate; alkyl citrate and citrate esters such as trimethyl citrate, triethyl citrate, tributyl citrate, acetyl triethyl citrate, and trihexyl citrate; alkyl adipates such as dioctyl adipate, diethyl adipate, di(2-methylethyl)adipate, and dihexyl adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; and low molecular weight polyalkylene glycols (molecular weight 300 to 600) such as polyethylene glycol 400; and mixtures thereof.

The amount of the plasticizer present in the composition will depend on the degree of tack desired, but generally represents in the range of about 25 wt. % to 45 wt. %, preferably about 25 wt. % to 40 wt. %, optimally about 30 wt. %, of the composition after drying.

3. The Tackifying Resin

The tackifying resin is a relatively low molecular weight resin (weight average molecular weight generally less than about 50,000) having a fairly high glass transition temperature. Tackifying resins include, for example, rosin derivatives, terpene resins, and synthetic or naturally derived petroleum resins. Preferred tackifying resins herein are generally selected from the group of non-polar tackifying resins, such as Regalrez® 1085 (a hydrogenated hydrocarbon resin) and Regalite® Resins such as Regalite® 1900, available from Hercules, Escorez 1304 (also a hydrocarbon resins) and Escorez® 1102 available from Exxon Chemical Company, Wingtack® 95 (a synthetic polyterpene resin), or Wingtack® 85, available from Goodyear Tire and Rubber. The resin represents approximately 5 wt. % to about 15 wt. %, preferably 7.5 wt. % to 12 wt. %, and preferably 7.5 wt. % to 10 wt. %, relative to the dry hydrogel composition. If increased adhesion is desired, a greater quantity of the resin should be used. Ideally, the weight ratio of the resin to the hydrophobic PSA is in the range of approximately 40:60 to 60:40.

4. The Optional Antioxidant

Incorporation of an antioxidant is optional but preferred. The antioxidant serves to enhance the oxidative stability of the hydrogel composition. Heat, light, impurities, and other factors can all result in oxidation of the hydrogel composition. Thus, ideally, antioxidants should protect against light-induced oxidation, chemically induced oxidation, and thermally induced oxidative degradation during processing and/or storage. Oxidative degradation, as will be appreciated by those in the art, involves generation of peroxy radicals, which in turn react with organic materials to form hydroperoxides. Primary antioxidants are peroxy free radical scavengers, while secondary antioxidants induce decomposition of hydroperoxides, and thus protect a material from degradation by hydroperoxides. Most primary antioxidants are sterically hindered phenols, and preferred such compounds for use herein are tetrakis [methylene (3,5-di-tert-butyl-4-hydroxyhydrocinnamate)]methane (e.g., Irganox® 1010, from Ciba-Geigy Corp., Hawthorne, N.Y.) and 1,3,5-trimethyl-2,4,6-tris [3,5-di-t-butyl-4-hydroxy-benzyl]benzene (e.g., Ethanox® 330, from Ethyl Corp.). A particularly preferred secondary antioxidant that may replace or supplement a primary antioxidant is tris(2,4-di-tert-butylphenyl)phosphite (e.g., Irgafos® 168, Ciba-Geigy Corp.). Other antioxidants, including but not limited to multi-functional antioxidants, are also useful herein. Multifunctional antioxidants serve as both a primary and a secondary antioxidant. Irganox® 1520 D, manufactured by Ciba-Geigy is one example of a multifunctional antioxidant. Vitamin E antioxidants, such as that sold by Ciba-Geigy as Irganox® E17, are also useful in the present hydrogel compositions. Other suitable antioxidants include, without limitation, ascorbic acid, ascorbic palmitate, tocopherol acetate, propyl gallate, butylhydroxyanisole (BHA), butylated hydroxytoluene (BHT), bis(1,2,2,6,6-pentamethyl-4-piperidinyl)-(3,5-di-tert-butyl-4-hydroxybenzyl)butylpropanedioate, (available as Tinuvin®144 from Ciba-Geigy Corp.) or a combination of octadecyl 3,5-di-tert-butyl-4-hydroxyhydrocinnamate (also known as octadecyl 3-(3',5'-di-tert-butyl-4'-hydroxyphenyl)propionate) (available as Naugard® 76 from Uniroyal Chemical Co., Middlebury, Conn.) and bis(1,2,2,6,6-pentamethyl-4-piperidinylsebacate) (available as Tinuvin® 765 from Ciba-Geigy Corp.). Preferably, the antioxidant is present in amount up to about 2 wt. % of the hydrogel composition; typically, the amount of antioxidant is in the range of about 0.05 wt. % to 1.5 wt. %.

B. The Discontinuous Hydrophilic Phase

The discontinuous hydrophilic phase represents on the order of 25 wt. % to 65 wt. %, preferably 30 wt. % to 55 wt. %, most preferably 30 wt. % to 40 wt. % of the dry hydrogel composition, and is comprised of a crosslinked hydrophilic polymer that is insoluble in water under standard conditions of storage and use, but is water-swellable. The degree of crosslinking is selected so that the polymer will not melt during manufacture of the composition, ensuring that the hydrophilic phase remains discontinuous in the final product. Suitable polymers for the discontinuous hydrophilic phase include, but are not limited to: crosslinked cellulosic polymers (such as crosslinked sodium carboxymethylcellulose); crosslinked acrylate polymers and copolymers; carbomers, i.e., hydroxylated vinylic polymers also referred to as "interpolymers," which are prepared by crosslinking a monoolefinic acrylic acid monomer with a polyalkyl ether of sucrose (commercially available under the trademark Carbopol® from the B.F. Goodrich Chemical Company); crosslinked acrylamide-sodium acrylate copolymers; gelatin; vegetable polysaccharides, such as alginates, pectins, carrageenans, or xanthan; starch and starch derivatives; and galactomannan and galactomannan derivatives.

Preferred polymers suitable for forming the discontinuous hydrophilic phase are based on polysaccharides, either natural or synthetic. Materials of this class include, e.g., crosslinked, normally water-soluble cellulose derivatives that are crosslinked to provide water-insoluble, water-swellable compounds, such as crosslinked sodium carboxymethylcellulose (CMC), crosslinked hydroxyethyl cellulose (HEC), crosslinked partial free acid CMC, and guar gum grafted with acrylamide and acrylic acid salts in combination with divinyl compounds, e.g., methylene-bis acrylamide. Within the aforementioned class, the more preferred materials are crosslinked CMC derivatives, particularly crosslinked sodium CMC and crosslinked HEC.

Sodium CMC can be cross-linked with any of a number of reagents that are difunctional with respect to cellulose. Crosslinking methods applicable to sodium CMC are discussed in, e.g., U.S. Pat. Nos. 3,168,421 and 3,589,364. Reagents that are difunctional with respect to cellulose include formaldehyde, epichlorohydrin and diepoxide reagents. Epichlorohydrin is a particularly useful crosslinker. Cross-linking can be accomplished by either the wet or dry method taught in the referenced patents. Either technique produces a water-insoluble but water-swellable polymer.

Crosslinked sodium CMC can also be provided without need for a crosslinking agent, by partial acidification of the uncrosslinked, esterified polymer (i.e., sodium CMC itself) to prepare "partial free acid CMC," followed by drying. During the drying process, the free acidic groups of the partial free acid CMC crosslink via an internal esterification reaction, as described, for example, in U.S. Pat. No. 4,128,692. Preparation of partial free acid CMC is known in the art, and described in U.S. Pat. No. 3,379,720.

A particularly preferred crosslinked hydrophilic polymer is crosslinked sodium CMC, available as Aquasorb® A500 from Aqualon, a division of Hercules, Inc.

C. Optional Additives

The hydrogel composition may also include conventional additives such as fillers, preservatives, pH regulators, softeners, thickeners, pigments, dyes, refractive particles, stabilizers, toughening agents, detackifiers, pharmaceutical agents, and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the hydrogel composition.

Absorbent fillers may be advantageously incorporated to control the degree of hydration when the adhesive is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon. A preferred filler is colloidal silica, e.g., Cab-O-Sil® (Cabot Corporation, Boston Mass.).

Preservatives include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

Compounds useful as pH regulators include, but are not limited to, glycerol buffers, citrate buffers, borate buffers, phosphate buffers, or citric acid-phosphate buffers may also be included so as to ensure that the pH of the hydrogel composition is compatible with that of an individual's body surface.

Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

Suitable pharmacologically active agents and optional permeation enhancers are described in Section V, infra.

III. Hydrogel Compositions with a Discontinuous Hydrophobic Phase and a Continuous Hydrophilic Phase In an alternative embodiment, a hydrogel composition is provided that is comprised of:

(a) a hydrophobic discontinuous phase comprising
    (i) a hydrophobic polymer,
    (ii) a plasticizer, preferably elastomeric,
    (iii) a tackifying resin, and
    (iv) an optional antioxidant; and
  (b) a continuous hydrophilic phase comprising:
    (i) a water-swellable, water-insoluble polymer,
    (ii) a blend of a hydrophilic polymer and a complementary oligomer capable of hydrogen bonding thereto, and
    (iii) an optional low molecular weight plasticizer.

In this embodiment, the components of the hydrophobic discontinuous phase are as described in Section II, and the optional additives discussed therein may be present in this embodiment as well. Here, however, the hydrophilic phase is continuous rather than discontinuous, and is comprised of the following components: a water-swellable, water-insoluble polymer; a blend of a hydrophilic polymer and a complementary oligomer capable of hydrogen bonding thereto; and an optional low molecular weight plasticizer.

The water-swellable, water-insoluble polymer is capable of at least some degree of swelling when immersed in an aqueous liquid but is insoluble in water within a selected pH range, generally up to a pH of at least about 7.5 to 8.5. The polymer may be comprised of a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049, 1,683,347, 1,880,808, 1,880,560, 1,984,147, 2,129,052, and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000.

Generally, the cellulose ester comprises a mixture of cellulose and cellulose ester monomer units; for example, commercially available cellulose acetate butyrate contains cellulose acetate monomer units as well as cellulose butyrate monomer units and unesterified cellulose units. Preferred cellulose esters herein are cellulose acetate propionate compositions and cellulose acetate butyrate compositions having the butyryl, propionyl, acetyl, and unesterified (OH) cellulose content as indicated below:

Eudragit L-30D-55 and Eudragit L-100-55 (the latter copolymer is a spray-dried form of Eudragit L-30D-55 that can be reconstituted with water). The molecular weight of the Eudragit L-30D-55 and Eudragit L-100-55 copolymer is approximately 135,000 Da, with a ratio of free carboxyl groups to ester groups of approximately 1:1. The copolymer is generally insoluble in aqueous fluids having a pH below 5.5. Another particularly suitable methacrylic acid-methyl methacrylate copolymer is Eudragit S-100, which differs from Eudragit L-30D-55 in that the ratio of free carboxyl groups to ester groups is approximately 1:2. Eudragit S-100 is insoluble at pH below 5.5, but unlike Eudragit L-30D-55, is poorly soluble in aqueous fluids having a pH in the range of 5.5 to 7.0. This copolymer is soluble at pH 7.0 and above. Eudragit L-100 may also be used, which has a pH-dependent solubility profile between that of Eudragit L-30D-55 and Eudragit S-100, insofar as it is insoluble at a pH below 6.0. It will be appreciated by those skilled in the art that Eudragit L-30D-55, L-100-55, L-100, and S-100 can be replaced with other acceptable polymers having similar pH-dependent solubility characteristics.

The second component of the continuous hydrophilic phase is a blend of a hydrophilic polymer and a complementary oligomer capable of hydrogen bonding to the hydrophilic polymer, and optionally capable of ionically or covalently bonding to the hydrophilic polymer as well. Suitable hydrophilic polymers include repeating units derived from an N-vinyl lactam monomer, a carboxy vinyl monomer, a vinyl ester monomer, an ester of a carboxy vinyl monomer, a vinyl amide monomer, and/or a hydroxy vinyl monomer. Such polymers include, by way of example, poly(N-vinyl lactams), poly(N-vinyl acrylamides), poly(N-alkylacrylamides), substituted and unsubstituted acrylic and methacrylic acid polymers,

|  | Butyrate (%) | Acetyl (%) | OH (%) | MW (g/mole) | $T_g$ (° C.) | $T_m$ (° C.) |
|---|---|---|---|---|---|---|
| Cellulose Acetate Butyrate | 17-52 | 2.0-29.5 | 1.1-4.8 | 12,000-70,000 | 96-141 | 130-240 |
|  | Propionate (%) |  |  |  |  |  |
| Cellulose Acetate Propionate | 42.5-47.7 | 0.6-1.5 | 1.7-5.0 | 15,000-75,000 | 142-159 | 188-210 |

The preferred molecular weight, glass transition temperature ($T_g$) and melting temperature ($T_m$) are also indicated. Also, suitable cellulosic polymers typically have an inherent viscosity (I.V.) of about 0.2 to about 3.0 deciliters/gram, preferably about 1 to about 1.6 deciliters/gram, as measured at a temperature of 25° C. for a 0.5 gram sample in 100 ml of a 60/40 by weight solution of phenol tetrachloroethane.

Other preferred water-swellable polymers are acrylate polymers, generally formed from acrylic acid, methacrylic acid, methyl acrylate, ethyl acrylate, methyl methacrylate, ethyl methacrylate, and/or other vinyl monomers. Suitable acrylate polymers are those copolymers available under the tradename "Eudragit" from Rohm Pharma (Germany), as indicated supra. The Eudragit series E, L, S, RL, RS and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are polyvinyl alcohol (PVA), polyvinylamine, copolymers thereof and copolymers with other types of hydrophilic monomers (e.g. vinyl acetate).

Poly(N-vinyl lactams) useful herein are preferably non-crosslinked homopolymers or copolymers of N-vinyl lactam monomer units, with N-vinyl lactam monomer units representing the majority of the total monomeric units of a poly (N-vinyl lactams) copolymer. Preferred poly(N-vinyl lactams) for use in conjunction with the invention are prepared by polymerization of one or more of the following N-vinyl lactam monomers: N-vinyl-2-pyrrolidone; N-vinyl-2-valerolactam; and N-vinyl-2-caprolactam. Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

Poly(N-alkylacrylamides) include, by way of example, poly(methacrylamide) and poly(N-isopropyl acrylamide) (PNIPAM).

Polymers of carboxy vinyl monomers are typically formed from acrylic acid, methacrylic acid, crotonic acid, isocrotonic acid, itaconic acid and anhydride, a 1,2-dicarboxylic acid such as maleic acid or fumaric acid, maleic anhydride, or mixtures thereof, with preferred hydrophilic polymers within this class including polyacrylic acid and polymethacrylic acid, with polyacrylic acid most preferred.

Preferred hydrophilic polymers herein are the following: poly(N-vinyl lactams), particularly polyvinyl pyrrolidone (PVP) and poly(N-vinyl caprolactam) (PVCap); poly(N-vinyl acetamides), particularly polyacetamide per se; polymers of carboxy vinyl monomers, particularly polyacrylic acid and polymethacrylic acid; and copolymers and blends thereof. PVP and PVCap are particularly preferred.

The molecular weight of the hydrophilic polymer is not critical; however, the number average molecular weight of the hydrophilic polymer is generally in the range of approximately 100,000 to 2,000,000, more typically in the range of approximately 500,000 to 1,500,000. The oligomer is "complementary" to the hydrophilic polymers in that it is capable of hydrogen bonding thereto. Preferably, the complementary oligomer is terminated with hydroxyl groups, amino or carboxyl groups. The oligomer typically has a glass transition temperature $T_g$ in the range of about −100° C. to about −30° C. and a melting temperature $T_m$ lower than about 20° C. The oligomer may be also amorphous. The difference between the $T_g$ values the hydrophilic polymer and the oligomer is preferably greater than about 50° C., more preferably greater than about 100° C., and most preferably in the range of about 150° C. to about 300° C. The hydrophilic polymer and complementary oligomer should be compatible, i.e. capable of forming a homogeneous blend that exhibits a single $T_g$, intermediate between those of the unblended components. Generally, the oligomer will have a molecular weight in the range from about 45 to about 800, preferably in the range of about 45 to about 600. Examples of suitable oligomers include, but are not limited to, low molecular weight polyalcohols (e.g. glycerol), oligoalkylene glycols such as ethylene glycol and propylene glycol, ether alcohols (e.g., glycol ethers), alkane diols from butane diol to octane diol, including carboxyl-terminated and amino-terminated derivatives of polyalkylene glycols. Polyalkylene glycols, optionally carboxyl-terminated, are preferred herein, and polyethylene glycol having a molecular weight in the range of about 300 to 600 is an optimal complementary oligomer.

It will be appreciated from the foregoing that a single compound, e.g., a low molecular weight polyalkylene glycol such as polyethylene glycol having a molecular weight in the range of about 300 to 600, can serve as both the complementary oligomer and the low molecular weight plasticizer.

As discussed in co-pending application Ser. No. 09/900,697 for "Preparation of Hydrophilic Pressure Sensitive Adhesives Having Optimized Adhesive Properties," filed on Jul. 6, 2001 (published as U.S. Patent Publication No. 2002/0037977 on Mar. 28, 2002), the ratio of the hydrophilic polymer to the complementary oligomer in the aforementioned blend affects both adhesive strength and the cohesive strength. As explained in the aforementioned patent application, the complementary oligomer decreases the glass transition of the hydrophilic polymer/complementary oligomer blend to a greater degree than predicted by the Fox equation, which is given by equation (1)

$$\frac{1}{T_{g\,predicted}} = \frac{w_{pol}}{T_{g_{pol}}} + \frac{w_{pl}}{T_{g_{pl}}} \qquad (1)$$

where $T_{g\,predicted}$ is the predicted glass transition temperature of the hydrophilic polymer/complementary oligomer blend, $W_{pol}$ is the weight fraction of the hydrophilic polymer in the blend, $w_{pl}$ is the weight fraction of the complementary oligomer in the blend, $T_{g\,pol}$ is the glass transition temperature of the hydrophilic polymer, and $T_{g\,pl}$ is the glass transition temperature of the complementary oligomer. As also explained in that patent application, an adhesive composition having optimized adhesive and cohesive strength can be prepared from a hydrophilic polymer and a complementary oligomer by selecting the components and their relative amounts to give a predetermined deviation from $T_{g\,predicted}$. Generally, to maximize adhesion, the predetermined deviation from $T_{g\,predicted}$ will be the maximum negative deviation, while to minimize adhesion, any negative deviation from $T_{g\,predicted}$ is minimized. Optimally, the complementary oligomer represents approximately 25 wt. % to 75 wt. %, preferably about 30 wt. % to about 60 wt. %, of the hydrophilic polymer/complementary oligomer blend, and, correspondingly, the hydrophilic polymer represents approximately 75 wt. % to 25 wt. %, preferably about 70 wt. % to about 40 wt. %, of the hydrophilic polymer/oligomer blend.

As the complementary oligomer itself acts as a plasticizer, it is not generally necessary to incorporate an added plasticizer. However, inclusion of an additional low molecular weight plasticizer in the composition is optional and may, in some cases, be advantageous. Suitable low molecular weight plasticizers include those set forth in Section II.A.2, i.e.: dialkyl phthalates, dicycloalkyl phthalates, diaryl phthalates and mixed alkyl-aryl phthalates as represented by dimethyl phthalate, diethyl phthalate, dipropyl phthalate, di(2-ethylhexyl)-phthalate, di-isopropyl phthalate, diamyl phthalate and dicapryl phthalate; alkyl and aryl phosphates such as tributyl phosphate, trioctyl phosphate, tricresyl phosphate, and triphenyl phosphate; alkyl citrate and citrate esters such as trimethyl citrate, triethyl citrate, tributyl citrate, acetyl triethyl citrate, and trihexyl citrate; dialkyl adipates such as dioctyl adipate (DOA; also referred to as bis(2-ethylhexyl) adipate), diethyl adipate, di(2-methylethyl)adipate, and dihexyl adipate; dialkyl tartrates such as diethyl tartrate and dibutyl tartrate; dialkyl sebacates such as diethyl sebacate, dipropyl sebacate and dinonyl sebacate; dialkyl succinates such as diethyl succinate and dibutyl succinate; alkyl glycolates, alkyl glycerolates, glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; and mixtures thereof. Preferred low molecular weight plasticizers for the continuous hydrophilic phase are triethyl citrate, diethyl phthalate, and dioctyl adipate, with dioctyl adipate most preferred.

With the proper ratio of the water-swellable, water-insoluble polymer, low molecular weight plasticizer, and hydrophilic polymer/complementary oligomer blend, the hydrogel composition in this embodiment can be made translucent. Specifically, the relative amount of each component should be as follows in order to achieve a translucent composition:

water-swellable, water-insoluble polymer, about 2 wt. % to 15 wt. %, preferably, for cellulose esters, about 5 wt. % to 15 wt. %;

low molecular weight plasticizer, about 2.5 wt. % to 5.0 wt. %; and hydrophilic polymer/complementary oligomer blend, about 17.5 wt. % to 45 wt. %.

IV. Hydrogel Compositions Composed of a Continuous Hydrophilic Phase

In another embodiment, the hydrogel composition does not contain a hydrophobic phase, but instead is entirely comprised of a continuous hydrophilic phase, although optional additives may be included as discussed in Section II.B. The hydrophilic phase includes a water-swellable, water-insoluble polymer as described in Section III, a blend of a hydrophilic polymer and a complementary oligomer that can serve as a low molecular weight plasticizer, and, optionally, an additional low molecular weight plasticizer. In this embodiment, the hydrophilic polymer in the blend is as described in Section III, and the complementary oligomer is a low molecular weight polyalkylene glycol (molecular weight 300-600) such as polyethylene glycol 400, and can also serve as a low molecular weight plasticizer. Alternatively, a different compound can be incorporated as an additional low molecular weight plasticizer, in which case any of the low molecular weight plasticizers described in Section III can be used.

The water-swellable, water-insoluble polymer is preferably a cellulose ester or an acrylic acid or acrylate polymer or copolymer, as described in Section III. However, for these hydrogel compositions, when prepared using a solution casting technique, the water-swellable, water-insoluble polymer should be selected to provide greater cohesive strength and thus facilitate film forming (generally, for example, cellulose acetate propionate tends to improve cohesive strength to a greater degree than cellulose acetate butyrate).

Optimally, to achieve translucence, the relative amounts of each component in the hydrogel composition are as follows:
water-swellable, water-insoluble polymer, about 30 wt. % to 40 wt. %; hydrophilic polymer, about 25 wt. % to 30 wt. %.

low molecular weight plasticizer and/or complementary oligomer, about 30 wt. % to 35 wt. %.

In this embodiment, when the water-swellable polymer is an acrylic acid or acrylate polymer, a hydrogel is provided that can be reversibly dried, i.e., after removal of water and any other solvents, the dried hydrogel may be reconstituted to its original state by addition of water. In addition, hydrophilic hydrogels prepared with an acrylic acid/acrylate waterswellable polymer are generally substantially nontacky prior to contact with water, but become tacky upon contact with a moist surface. This property enables positioning or repositioning on a surface before or as the hydrogel becomes tacky and adheres to the surface. In addition, acrylate-containing compositions can generally provide swelling in the range of about 400% to 1500% upon immersion of the hydrogel composition in water or other aqueous liquid, at a pH of less than 8.5, although the ratio of the acrylate polymer to the hydrophilic polymer/complementary oligomer blend can be selected so as that the rate and extent of swelling in an aqueous environment has a predetermined pH-dependence.

By contrast, incorporating a cellulose ester as the waterswellable polymer renders the hydrogel tacky prior to application to a moist surface, but nontacky upon absorption of water. It will be appreciated that such a composition is particularly useful in a wound dressing, where a decrease in tack is desired for ultimate removal of the product from a wound.

V. Hydrogel Compositions Containing an Active Agent

Any of the above-described hydrogel compositions may be modified so as to contain an active agent and thereby act as an active agent delivery system when applied to a body surface in active agent-transmitting relation thereto. The release of active agents "loaded" into the present hydrogel compositions typically involves both absorption of water and desorption of the agent via a swelling-controlled diffusion mechanism. Active agent-containing hydrogel compositions may be employed, by way of example, in transdermal drug delivery systems, in wound dressings, in topical pharmaceutical formulations, in implanted drug delivery systems, in oral dosage forms, and the like.

Suitable active agents that may be incorporated into the present hydrogel compositions and delivered systemically (e.g., with a transdermal, oral, or other dosage form suitable for systemic administration of a drug) include, but are not limited to: analeptic agents; analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, antianginal agents, central nervous system (CNS) agents, beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids, including progestogens, estrogens, corticosteroids, androgens and anabolic agents; smoking cessation agents; sympathomimetics; tranquilizers; and vasodilators including general coronary, peripheral and cerebral. Specific active agents with which the present adhesive compositions are useful include, without limitation, anabasine, capsaicin, isosorbide dinitrate, aminostigmine, nitroglycerine, verapamil, propranolol, silabolin, foridone, clonidine, cytisine, phenazepam, nifedipine, fluacizin, and salbutamol.

For topical drug administration and/or medicated cushions (e.g., medicated footpads), suitable active agents include, by way of example, the following:

Bacteriostatic and bactericidal agents: Suitable bacteriostatic and bactericidal agents include, by way of example: halogen compounds such as iodine, iodopovidone complexes (i.e., complexes of PVP and iodine, also referred to as "povidine" and available under the tradename Betadine® from Purdue Frederick), iodide salts, chloramine, chlorhexidine, and sodium hypochlorite; silver and silver-containing compounds such as sulfadiazine, silver protein acetyltannate, silver nitrate, silver acetate, silver lactate, silver sulfate and silver chloride; organotin compounds such as tri-n-butyltin benzoate; zinc and zinc salts; oxidants, such as hydrogen peroxide and potassium permanganate; aryl mercury compounds, such as phenylmercury borate or merbromin; alkyl mercury compounds, such as thiomersal; phenols, such as thymol, o-phenyl phenol, 2-benzyl-4-chlorophenol, hexachlorophen and hexylresorcinol; and organic nitrogen compounds such as 8-hydroxyquinoline, chlorquinaldol, clioquinol, ethacridine, hexetidine, chlorhexedine, and ambazone.

Antibiotic agents: Suitable antibiotic agents include, but are not limited to, antibiotics of the lincomycin family (referring to a class of antibiotic agents originally recovered from *streptomyces lincolnensis*), antibiotics of the tetracycline family (referring to a class of antibiotic agents originally recovered from *streptomyces aureofaciens*), and sulfur-based antibiotics, i.e., sulfonamides. Exemplary antibiotics of the lincomycin family include lincomycin itself (6,8-dideoxy-6-[[(1-methyl-4-propyl-2-pyrrolidinyl)-carbonyl]amino]-1-thio-L-threo-α-D-galactooctopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]amino]-1-thio-L-threo-α-D-galacto-octopyranoside), related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself 4-(dimethylamino)-1,4,4α,5,5α,6,11,12α-octahydro-3,6,12,12α-pentahydroxy-6-methyl-1,1'-dioxo-2-naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium.

Pain relieving agents: Suitable pain relieving agents are local anesthetics, including, but not limited to, acetamidoeugenol, alfadolone acetate, alfaxalone, amucaine, amolanone, amylocalne, benoxinate, betoxycaine, biphenamine, bupivacaine, burethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocalne, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and combinations thereof. Tetracaine, lidocaine and prilocalne are referred pain relieving agents herein.

Other topical agents that may be delivered using the present hydrogel compositions as drug delivery systems include the following: antifungal agents such as undecylenic acid, tolnaftate, miconazole, griseofulvine, ketoconazole, ciclopirox, clotrimazole and chloroxylenol; keratolytic agents, such as salicylic acid, lactic acid and urea; vessicants such as cantharidin; anti-acne agents such as organic peroxides (e.g., benzoyl peroxide), retinoids (e.g., retinoic acid, adapalene, and tazarotene), sulfonamides (e.g., sodium sulfacetamide), resorcinol, corticosteroids (e.g., triamcinolone), alpha-hydroxy acids (e.g., lactic acid and glycolic acid), alpha-keto acids (e.g., glyoxylic acid), and antibacterial agents specifically indicated for the treatment of acne, including azelaic acid, clindamycin, erythromycin, meclocycline, minocycline, nadifloxacin, cephalexin, doxycycline, and ofloxacin; skin-lightening and bleaching agents, such as hydroquinone, kojic acid, glycolic acid and other alpha-hydroxy acids, artocarpin, and certain organic peroxides; agents for treating warts, including salicylic acid, imiquimod, dinitrochlorobenzene, dibutyl squaric acid, podophyllin, podophyllotoxin, cantharidin, trichloroacetic acid, bleomycin, cidofovir, adefovir, and analogs thereof, and anti-inflammatory agents such as corticosteroids and nonsteroidal anti-inflammatory drugs (NSAIDs), where the NSAIDS include ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, and tiaprofenic acid.

For wound dressings, suitable active agents are those useful for the treatment of wounds, and include, but are not limited to bacteriostatic and bactericidal compounds, antibiotic agents, pain relieving agents, vasodilators, tissue-healing enhancing agents, amino acids, proteins, proteolytic enzymes, cytokines, and polypeptide growth factors. Specific such agents are set forth in Section IX, infra.

For topical and transdermal administration of some active agents, and in wound dressings, it may be necessary or desirable to incorporate a permeation enhancer into the hydrogel composition in order to enhance the rate of penetration of the agent into or through the skin. Suitable enhancers include, for example, the following: sulfoxides such as dimethylsulfoxide (DMSO) and decylmethylsulfoxide ($C_{10}$MSO); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclaza-cycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. Mixtures of two or more enhancers may also be used.

VI. Conductive Hydrogel Compositions

The hydrogel compositions of the invention can be rendered electrically conductive for use in biomedical electrodes and other electrotherapy contexts, i.e., to attach an electrode or other electrically conductive member to the body surface. For example, the hydrogel composition, formulated so as to exhibit pressure-sensitive adhesion, may be used to attach a transcutaneous nerve stimulation electrode, an electrosurgical return electrode, or an EKG electrode to a patient's skin or mucosal tissue. These applications involve modification of the hydrogel composition so as to contain a conductive species. Suitable conductive species are ionically conductive electrolytes, particularly those that are normally used in the manufacture of conductive adhesives used for application to the skin or other body surface, and include ionizable inorganic salts, organic compounds, or combinations of both. Examples of ionically conductive electrolytes include, but are not limited to, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate and potassium chloride, and redox couples such as a mixture of ferric and ferrous salts such as sulfates and gluconates. Preferred salts are potassium chloride, sodium chloride, magnesium sulfate, and magnesium acetate, and potassium chloride is most preferred for EKG applications. Although virtually any amount of electrolyte may be present in the adhesive compositions of the invention, it is preferable that any electrolyte present be at a concentration in the range of about 0.1 to about 15 wt. % of the hydrogel composition. The procedure described in U.S. Pat. No. 5,846,558 to Nielsen et al. for fabricating biomedical electrodes may be adapted for use with the hydrogel compositions of the invention, and the disclosure of that patent is incorporated by reference with respect to manufacturing details. Other suitable fabrication procedures may be used as well, as will be appreciated by those skilled in the art.

VII. Crosslinking and High Cohesive Strength Hydrogel Compositions

For certain applications, particularly when high cohesive strength is desired (such as with pressure-relieving cushions), the hydrophilic polymer and optionally the complementary oligomer in the continuous hydrophilic phase (i.e., in the hydrogel compositions described in Sections III and IV) may be covalently crosslinked. The hydrophilic polymer may be covalently crosslinked, either intramolecularly or intermolecularly, and/or the hydrophilic polymer and the complementary oligomer may be covalently crosslinked. In the former case, there are no covalent bonds linking the hydrophilic polymer to the complementary oligomer, while in the latter case, there are covalent crosslinks binding the hydrophilic polymer to the complementary oligomer. The hydrophilic polymer, or the hydrophilic polymer and the complementary oligomer, may be covalently crosslinked using heat, radiation, or a chemical curing (crosslinking) agent. The degree of crosslinking should be sufficient to eliminate or at least minimize cold flow under compression.

For thermal crosslinking, a free radical polymerization initiator is used, and can be any of the known free radical-generating initiators conventionally used in vinyl polymerization. Preferred initiators are organic peroxides and azo compounds, generally used in an amount from about 0.01 wt. % to 15 wt. %, preferably 0.05 wt. % to 10 wt. %, more preferably from about 0.1 wt. % to about 5% and most preferably from about 0.5 wt. % to about 4 wt. % of the polymerizable material. Suitable organic peroxides include dialkyl peroxides such as t-butyl peroxide and 2,2 bis(t-butylperoxy) propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. Suitable azo compounds include azo bis (isobutyronitrile) and azo bis(2,4-dimethylvaleronitrile). The temperature for thermally crosslinking will depend on the actual components and may be readily deduced by one of ordinary skill in the art, but typically ranges from about 80° C. to about 200° C.

Crosslinking may also be accomplished with radiation, typically in the presence of a photoinitiator. The radiation may be ultraviolet, alpha, beta, gamma, electron beam, and x-ray radiation, although ultraviolet radiation is preferred. Useful photosensitizers are triplet sensitizers of the "hydrogen abstraction" type, and include benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylaceto-phenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxy-carbonyl)-oxime, thioxanthones including alkyl- and halogen-substituted thioxanthonse such as 2-isopropylthioxanthone, 2-chlorothioxanthone, 2,4 dimethyl thioxanone, 2,4 dichlorothioxanone, and 2,4-diethyl thioxanone, and acyl phosphine oxides. Radiation having a wavelength of 200 to 800 nm, preferably, 200 to 500 nm, is preferred for use herein, and low intensity ultraviolet light is sufficient to induce crosslinking in most cases. However, with photosensitizers of the hydrogen abstraction type, higher intensity UV exposure may be necessary to achieve sufficient crosslinking. Such exposure can be provided by a mercury lamp processor such as those available from PPG, Fusion, Xenon, and others. Crosslinking may also be induced by irradiating with gamma radiation or an electron beam. Appropriate irradiation parameters, i.e., the type and dose of radiation used to effect crosslinking, will be apparent to those skilled in the art.

Suitable chemical curing agents, also referred to as chemical cross-linking "promoters," include, without limitation, polymercaptans such as 2,2-dimercapto diethylether, dipentaerythritol hexa(3-mercaptopropionate), ethylene bis(3-mercaptoacetate), pentaerythritol tetra(3-mercaptopropionate), pentaerythritol tetrathioglycolate, polyethylene glycol dimercaptoacetate, polyethylene glycol di(3-mercaptopropionate), trimethylolethane tri(3-mercaptopropionate), trimethylolethane trithioglycolate, trimethylolpropane tri(3-mercapto-propionate), trimethylolpropane trithioglycolate, dithioethane, di- or trithiopropane and 1,6-hexane dithiol. The crosslinking promoter is added to the uncrosslinked hydrophilic polymer to promote covalent crosslinking thereof, or to a blend of the uncrosslinked hydrophilic polymer and the complementary oligomer, to provide crosslinking between the two components.

The hydrophilic polymer may also be crosslinked prior to admixture with the complementary oligomer. In such a case, it may be preferred to synthesize the polymer in crosslinked form, by admixing a monomeric precursor to the polymer with multifunctional comonomer and copolymerizing. Examples of monomeric precursors and corresponding polymeric products are as follows: N-vinyl amide precursors for a poly(N-vinyl amide) product; N-alkylacrylamides for a poly (N-alkylacrylamide) product; acrylic acid for a polyacrylic acid product; methacrylic acid for a polymethacrylic acid product; acrylonitrile for a poly(acrylonitrile) product; and N-vinyl pyrrolidone (NVP) for a poly(vinylpyrrolidone) (PVP) pro duct. Polymerization may be carried out in bulk, in suspension, in solution, or in an emulsion. Solution polymerization is preferred, and polar organic solvents such as ethyl acetate and lower alkanols (e.g., ethanol, isopropyl alcohol, etc.) are particularly preferred. For preparation of hydrophilic vinyl polymers, synthesis will typically take place via a free radical polymerization process in the presence of a free radical initiator as described above. The multifunctional comonomer include, for example, bisacrylamide, acrylic or methacrylic esters of diols such as butanediol and hexanediol (1,6-hexane diol diacrylate is preferred), other acrylates such as pentaerythritol tetraacrylate, and 1,2-ethylene glycol diacrylate, and 1,12-dodecanediol diacrylate. Other useful multifunctional crosslinking monomers include oligomeric and polymeric multifunctional (meth)acrylates, e.g., poly(ethylene oxide) diacrylate or poly(ethylene oxide) dimethacrylate; polyvinylic crosslinking agents such as substituted and unsubstituted divinylbenzene; and difunctional urethane acrylates such as EBECRYL® 270 and EBECRYL® 230 (1500 weight average molecular weight and 5000 weight average molecular weight acrylated urethanes, respectively—both available from UCB of Smyrna, Ga.), and combinations thereof. If a chemical crosslinking agent is employed, the amount used will preferably be such that the weight ratio of crosslinking agent to hydrophilic polymer is in the range of about 1:100 to 1:5. To achieve a higher crosslink density, if desired, chemical crosslinking is combined with radiation curing.

Any absorbent additives incorporated should be compatible with all components of the hydrogel-containing cushion, and should also serve to reduce or eliminate cold flow under compression. Suitable absorbent additives include, by way of example, polyacrylate starch derivatives, starches, starch copolymers, and the like.

VIII. Fabrication Processes

The hydrogel compositions of the invention are generally melt extrudable, and thus may be prepared using a simple blending and extruding process. The components of the composition are weighed out and then admixed, for example using a Brabender or Baker Perkins Blender, generally although not necessarily at an elevated temperature, e.g., about 90° C. to about 140° C. Solvents may be added. The resulting composition can be extruded using a single or twin extruder, or pelletized. Preferably the composition is extruded directly onto a substrate such as a backing layer or release liner, and then pressed. The thickness of the resulting hydrogel-containing film, for most purposes, will be in the range of about 0.20 mm to about 0.80 mm, more usually in the range of about 0.37 mm to about 0.47 mm.

Alternatively, the hydrogel compositions may be prepared by solution casting, by admixing the components of the composition in a suitable solvent, e.g., a volatile solvent such as ethanol, methanol, or isopropanol, at a concentration typically in the range of about 35% to 60% w/v. The solution is cast onto a substrate such as a backing layer or release liner, as above. Both admixture and casting are preferably carried out at ambient temperature. The substrate coated with the hydrogel film is then baked at a temperature in the range of about 80° C. to about 100° C., optimally about 90° C., for time period in the range of about one to four hours, optimally about two hours.

When tacky hydrogel compositions are desired, melt extrusion is the preferred process, although solution casting may still be used. For preparation of substantially nontacky hydrogel compositions, solution casting is preferred. Also, melt extrusion can be used for any of the hydrogel compositions of the invention, whether or not the compositions contain a hydrophobic phase, a continuous hydrophilic phase, or a discontinuous hydrophilic phase. Solution casting is generally although not necessarily limited to hydrogel compositions that are entirely composed of a hydrophilic phase. Also, either melt extrusion or solution casting techniques can be used to prepare translucent hydrogels, although solution casting is typically preferred.

IX. Wound Dressings

In a preferred embodiment, the hydrogel compositions of the invention are as absorbent materials in a wound dressing. In this embodiment, the hydrogel compositions are prepared so that they are substantially nontacky, or at most slightly tacky, when applied to the body surface. The hydrogel composition may be formulated so as to contain a pharmacologically active agent. Preferred active agents, in this embodiment, include the bacteriostatic and bactericidal agents, antibiotic agents, and pain-relieving agents set forth in Section V, as well as the following:

Topical Vasodilators: Such compounds are useful for increasing blood flow in the dermis, and preferred topical vasodilators are those known as rubefacients or counterirritants. Rubefacient agents include nicotinic acid, nicotinates such as methyl, ethyl, butoxyethyl, phenethyl and thurfyl nicotinate, as well as the essential oils such as mustard, turpentine, cajuput and *capsicum* oil, and components thereof. Particular preferred such compounds include, but are not limited to, methyl nicotinate, nicotinic acid, nonivamide, and capsaicin.

Proteolytic enzymes: Proteolytic enzymes herein are those that are effective wound cleansing agents, and include, for example, pepsin, trypsin, collagenase, chymotrypsin, elastase, carboxypeptidase, aminopeptidase, and the like.

Peptide, proteins, and amino acids: Suitable peptides and proteins are tissue-healing enhancing agents (also referred to in the art as "tissue regenerative agents") such as collagen, glycosaminoglycans (e.g., hyaluronic acid, heparin, heparin sulfate, chondroitin sulfate, etc.), proteoglycans (e.g., versican, biglycan) substrate adhesion molecules (e.g., fibronectin, vitronectin, laminin), polypeptide growth factors (e.g., platelet-derived growth factor, a fibroblast growth factor, a transforming growth factor, an insulin-like growth factor, etc.), and other peptides such as fibronectin, vitronectin, osteopontin, and thrombospondin, all of which contain the tripeptide sequence RGD (arginine-glycine-aspartic acid), a sequence generally associated with adhesive proteins and necessary for interaction with cell surface receptors.

One embodiment of a wound dressing of the invention is represented in FIG. 1. The wound dressing is generally indicated at 10, and comprises: an outer backing layer 12 that serves as the external surface of the dressing following application to the body surface; a skin contact adhesive layer 14 laminated thereto, which may or may not be an adhesive hydrogel composition of the invention, optionally containing one or more pharmacologically active agents; an absorbent wound-contacting region 16 comprised of a hydrogel composition of the invention and located on the on the wound contacting side of layer 14; and a removable release liner 18. Upon removable of the release liner, the dressing is applied to a body surface in the region of a wound, and placed on the body surface so that the wound-contacting region 16 is directly over the wound. In this embodiment, the wound dressing adheres to the skin surrounding the wound as a result of the exposed skin contact adhesive areas 20 and 22 surrounding the wound-contacting region. If the wound-contacting hydrogel composition is prepared so that it has some degree of tack prior to absorption of water (as in, e.g., wound exudate), the dressing adheres in the central region as well. It should be noted that any of the hydrogel compositions of the invention may be used as a wound dressing herein, providing that, as noted above, the hydrogel composition is substantially nontacky or at most slightly tacky. Also, those hydrogel compositions that exhibit a high degree of absorbency are preferred. The other components of the wound dressing of FIG. 1 are as follows:

The backing layer 12 of the wound dressing functions as the primary structural element and provides the dressing with flexibility. The material used for the backing layer should be inert and incapable of absorbing drug, enhancer or other components of the wound-contacting hydrogel composition. Also, the material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing. The layer is preferably although not necessarily nonocclusive (or "breathable"), i.e., is preferably permeable to moisture.

The skin contact adhesive layer 14 may be composed of a conventional pressure-sensitive adhesive such as may be selected from polysiloxanes, polyisobutylenes, polyacrylates, polyurethanes, polyisobutylene, and the like. Alternatively, the layer may be made from an adhesive hydrogel composition of the invention, as described in Sections II, III and IV, supra.

Release liner 18 is a disposable element that serves to protect the device prior to application. The release liner should be formed from a material impermeable to the drug, vehicle and adhesive, and that is easily stripped from the contact adhesive. Release liners are typically treated with silicone or fluorocarbons, and are commonly made from polyesters and polyethylene terephthalate.

Figure 2:
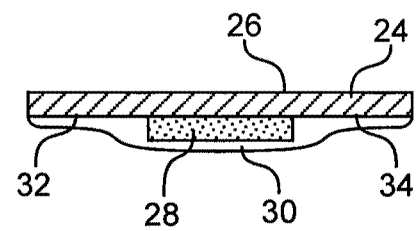
FIG. 2 schematically illustrates an alternative embodiment of a wound dressing of the invention that does not include separate backing and skin contact adhesive layers, wherein a backing layer is composed of a skin contact adhesive having a nontacky outwardly facing surface and a slightly tacky body facing surface, and a hydrogel composition of the invention is present as a film on an interior region of the body-contacting, at least slightly tacky surface of the backing layer.

In another embodiment, illustrated in FIG. 2, the backing layer 24 of the wound dressing shown is composed of a tacky or at least slightly tacky hydrogel composition of the invention, but is provided with a nontacky upper surface 26. The wound-contacting hydrogel material 28 is adhered to the skin-contacting side of the backing layer 24. Upon removal of release liner 30, the wound dressing is applied to an individual's skin in the region of a wound so that the wound-contacting hydrogel material is placed directly over the wound. As with the embodiment of FIG. 1, the wound dressing adheres to the body surface by virtue of the exposed regions 32 and 34 of the adhesive hydrogel composition. In this case, it is preferred that both the backing layer and the hydrogel be translucent, so that the extent of wound healing can be viewed directly through the backing, eliminating the need for frequent replacement or removal of the wound dressing.

Figure 3:
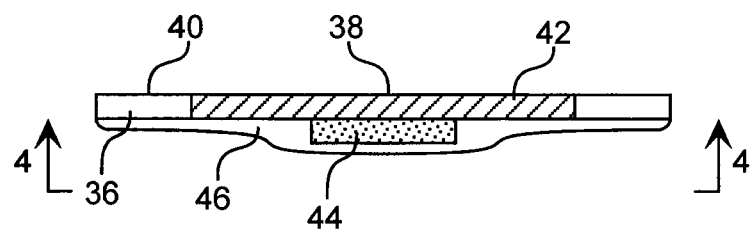
FIG. 3 schematically illustrates another embodiment of a wound dressing of the invention, wherein the dressing is similar in structure to that of FIG. 2, but includes a peripheral skin contact adhesive on the body-contacting surface. In this case, the body-contacting surface of the backing layer does not need to be tacky.

In a further embodiment, illustrated in FIG. 3, the perimeter 36 of the wound dressing is made of a different material than the interior region 38 of the backing. In this case, the perimeter 36 is comprised of a skin contact adhesive that may or may not be an adhesive hydrogel composition of the invention, although the upper, outwardly facing surface 40 of the perimeter is nontacky. The interior region 38 of the backing is preferably comprised of a hydrogel composition of the invention. The skin-facing side of the interior region 38 may or may not be tacky, although the upper surface 42 of the interior region 38 should be nontacky. The wound-contacting hydrogel material 44 is adhered to the underside (i.e., the skin contacting side) of the backing and is centrally located within interior region 38. As with the embodiment of FIG. 2, it is preferred that both the interior region 38 of the backing and the wound-contacting hydrogel material 44 are translucent. Generally, the perimeter adhesive will be opaque. The removable release liner is indicated at 46.

In a variation on the embodiment of FIG. 3, an outer layer may be laminated to the upper surface of the device shown. Such an outer layer would then serve as the actual backing, with the layer represented by interior region 38 and perimeter 36 representing an intermediate layer.

Figure 4:
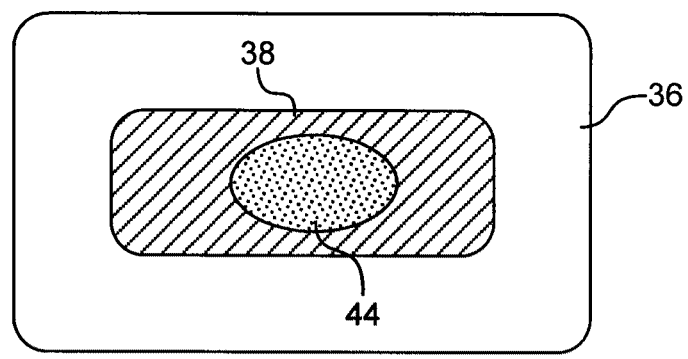
FIG. 4 is a bottom plan view of the embodiment of FIG. 3 taken along the 4-4 lines of that figure, and illustrates the concentric regions of the body-contacting surface, with a peripheral skin contact adhesive surrounding an inner region of a nontacky or slightly tacky material, which in turn contains the hydrogel composition in a central region intended as the wound-contacting region.

FIG. 4 is a bottom plan view of the wound dressing of FIG. 3 (with the release liner having been removed), taken along lines 4-4; the view shown is thus the skin-contacting face of the dressing. As described with respect to FIG. 3, the wound-contacting hydrogel material 44 is located within the interior region 38 of the backing, and the perimeter adhesive 36 surrounds that region.

Figure 5:
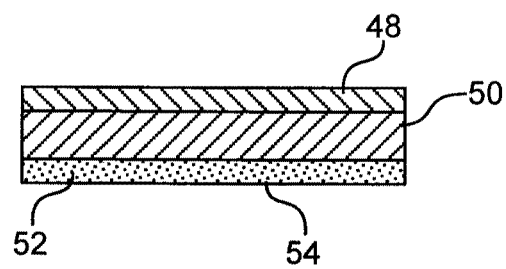
FIG. 5 illustrates another embodiment of a wound dressing herein wherein the three layers of a laminated composite, an outwardly facing backing layer, an interior pressure sensitive adhesive layer, and a body-contacting layer composed of a hydrogel composition of the invention, are coextensive.

In still another embodiment, illustrated in FIG. 5, the wound dressing contains three layers, a backing layer 48, a central adhesive layer 50 typically composed of a conventional pressure-sensitive adhesive, and a wound-contacting hydrogel layer 52, wherein the three layers are coextensive such that there is no distinct perimeter region as there is in the embodiments of FIG. 1 to 4. During storage and prior to use, the skin contacting side 54 of the dressing is protected with a release liner (not shown), as above.

Figure 6:
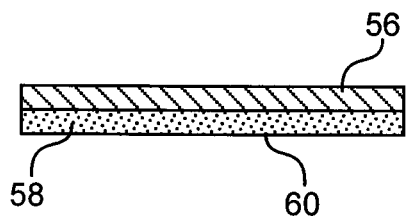
FIG. 6 illustrates an analogous embodiment wherein the interior pressure sensitive adhesive layer is omitted, and the hydrogel-containing layer is made sufficiently tacky so that the backing layer adheres directly thereto. Again, the backing layer and the body-contacting hydrogel layer are co-extensive.

FIG. 6 illustrates a variation of the embodiment of FIG. 5, wherein the wound dressing is composed of only two layers, a backing 56 and a wound-contacting hydrogel layer 58 laminated thereto and coextensive therewith. In this case, the hydrogel layer 58 must have sufficient tack so as to adhere to the backing layer, even after water absorption. As with the embodiments discussed above, the skin contacting side 60 is protected with a release liner (not shown) during storage and prior to use.

X. Active Agent Delivery Systems

An active agent may be delivered to a body surface by simply placing a hydrogel composition of the invention on a body surface in active agent-transmitting relation thereto. Alternatively, an active agent-containing hydrogel composition may be incorporated into a delivery system or "patch." In manufacturing such systems, the hydrogel adhesive composition may be cast or extruded onto a backing layer or release liner and will serve as the skin-contacting face of the system and act as an active agent reservoir. Alternatively, the hydrogel composition may be used as an active agent reservoir within the interior of such a system, with a conventional skin contact adhesive laminated thereto to affix the system to a patient's body surface.

Systems for the topical, transdermal or transmucosal administration of an active agent may comprise: (A) a reservoir containing a therapeutically effective amount of an active agent; (B) an adhesive means for maintaining the system in active agent transmitting relationship to a body surface; and (C) a backing layer as described in the preceding section, wherein (D) a disposable release liner covers the otherwise exposed adhesive, protecting the adhesive surface during storage and prior to use (also as described in the preceding section). In many such devices, the reservoir can also serve as the adhesive means, and the hydrogel compositions of the invention can be used as the reservoir and/or the adhesive means.

Any number of active agents can be administered using such delivery systems. Suitable active agents include the broad classes of compounds normally delivered to and/or through body surfaces and membranes; such active agents are described in Section V. With some active agents, it may be necessary to administer the agent along with a permeation enhancer in order to achieve a therapeutically effective flux through the skin. Suitable enhancers are also described in Section V.

Accordingly, an active agent-containing composition is incorporated into the reservoir, either during manufacture of the system or thereafter. The composition will contain a quantity of an active agent effective to provide the desired dosage over a predetermined delivery period. The composition will also contain a carrier (e.g., a vehicle to solubilize the active agent), a permeation enhancer, if necessary, and optional excipients such as colorants, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

Preferably, the delivery system is "monolithic," meaning that a single layer serves as both the active agent-containing reservoir and the skin contact adhesive. However, the reservoir and the skin contact adhesive may be separate and distinct layers. Also, more than one reservoir may be present, each containing a different component for delivery into the skin. The present hydrogel compositions may be used as any or all of the aforementioned layers.

The backing layer of the drug delivery system functions as the primary structural element of the transdermal system, and preferred backing materials in transdermal drug delivery devices are the same as those described in the preceding section with respect to wound dressings.

Additional layers, e.g., intermediate fabric layers and/or rate-controlling membranes, may also be present in a transdermal drug delivery system. Fabric layers may be used to facilitate fabrication of the device, while a rate-controlling membrane may be used to control the rate at which a component permeates out of the device. The component may be a drug, a permeation enhancer, or some other component contained in the drug delivery system.

In any of these systems, it may be desirable to include a rate-controlling membrane in the system on the body surface side of the drug reservoir. The materials used to form such a membrane are selected to limit the flux of one or more components contained in the drug formulation, and the membrane may be either microporous or dense. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

The compositions of the invention may also serve to deliver an active agent using other routes of administration. For example, the compositions may be formulated with excipients, carriers and the like suitable for oral administration of an orally active drug. The compositions may also be used in buccal and sublingual drug delivery, insofar as the compositions can adhere well to moist surfaces within the mouth. In buccal and sublingual systems, hydrolyzable and/or bioerodible polymers may be incorporated into the compositions to facilitate gradual erosion throughout a drug delivery period. Still other types of formulations and drug delivery platforms may be prepared using the present compositions, including implants, rectally administrable compositions, vaginally administrable compositions, and the like.

XI. Cushions and Other Products Requiring Adhesion to a Body Surface

The hydrogel compositions of the invention are useful in any number of additional contexts wherein adhesion of a product to a body surface is called for or desirable. These applications include, for example, pressure-relieving cushions for application to a foot, wherein the cushions may or may not contain medication for transdermal or topical delivery, e.g., in the treatment of dicubitis, veinous and diabetic foot ulcers, or the like. Suitable active agents are described in Section V.

Such cushions will generally be comprised of a flexible, resilient outer layer, fabricated from a foam pad or fabric, with a layer of an adhesive hydrogel composition of the invention laminated thereto for application to the skin surface. Suitable cushions include heel cushions, elbow pads, knee pads, shin pads, forearm pads, wrist pads, finger pads, corn pads, callus pads, blister pads, bunion pads and toe pads.

The hydrogel compositions of the invention are also useful in a host of other contexts, e.g., as adhesives for affixing medical devices, diagnostic systems and other devices to be affixed to a body surface, and in any other application wherein adhesion to a body surface is necessary or desired. The hydrogel compositions are also useful as sealants for ostomy devices, prostheses, and face masks, as sound, vibration or impact absorbing materials, as carriers in cosmetic and cosmeceutical gel products, and will have other uses known to or ascertainable by those of ordinary skill in the art, or as yet undiscovered.

The practice of the present invention will employ, unless otherwise indicated, conventional techniques of polymer chemistry, adhesive manufacture, and hydrogel preparation, which are within the skill of the art. Such techniques are fully explained in the literature.

It is to be understood that while the invention has been described in conjunction with the preferred specific embodiments thereof, the foregoing description, as well as the examples that follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in degrees Celsius (° C.), and pressure is at or near atmospheric.

The following abbreviations and tradenames are used in the examples:

Kalar® 5246: Crosslinked polyisobutylene, Mooney viscosity 30-40 cps at 25° C. (Elementis);
Kalar® 5215: Crosslinked polyisobutylene, Mooney viscosity 47-57 cps at 25° C. (Elementis);
Kalar® 5275: Crosslinked polyisobutylene, Mooney viscosity 70-75 cps at 25° C. (Elementis);
Styrene plasticizer: Styrene-isoprene copolymer (Kraton);
SBS Vector 6241: Styrene-butadiene-styrene copolymer (Exxon, styrene:butadiene ratio 43:57);
SIS Vector 4111: Styrene-isoprene-styrene copolymer (Exxon, styrene:isoprene ratio 18:82);
Regalite® 1900: Hydrocarbon resin (Hercules);

Irganox® 1010: Tetrakis [methylene (3,5-di-tert-butyl-4-hydroxyhydrocinnamate)]methane (Ciba-Geigy);

Aquasorb® A500: crosslinked sodium carboxymethylcellulose (Aqualon);

CAB 551-0.2: cellulose acetate butyrate having a butyryl content of 52 wt. %, an acetyl content of 2.0 wt. %, and a hydroxyl content of 1.8 wt. % (Eastman Chemical Co.);

CAB 553-0.4: cellulose acetate butyrate having a butyryl content of 46 wt. %, an acetyl content of 2.0 wt. %, and a hydroxyl content of 4.8 wt. % (Eastman Chemical Co.);

CAP 504-0.2: cellulose acetate propionate having a propionyl content of 42.5 wt. %, an acetyl content of 0.6 wt. %, and a hydroxyl content of 5.0 wt. % (Eastman Chemical Co.);

DOA: dioctyl adipate (bis-2-ethylhexyl)adipate, KIC Chemicals);

PVP: Kollidon® 90 polyvinylpyrrolidone (BASF);

PVCap: polyvinyl caprolactone (BASF);

PVP/PEG 400: a blend of Kollidon® 90 polyvinylpyrrolidone (BASF) and polyethylene glycol 400, 64:36 wt./wt. in ethanol (concentration 50%);

Cab-O-Sil®: Colloidal silica (Cabot);

BHA: butylhydroxyanisole.

Examples 1 and 2 describe the preparation of hydrogel compositions comprised of a discontinuous hydrophobic phase and a discontinuous hydrophilic phase using melt extrusion.

EXAMPLE 1

A hydrogel composition (designated 12SP-39) of a discontinuous hydrophobic phase and a discontinuous hydrophilic phase was prepared containing the following components:
Hydrophobic Phase:
Kalar 5246, 9.70 wt. %;
Styrene plasticizer, 29.12 wt. %;
SIS Vector 4111, 12.13 wt. %;
Regalite 1900, 9.70 wt. %;
Irganox 1010, 0.5 wt. %.
Hydrophilic Phase:
Aquasorb A500, 38.84 wt. %.
The above components were melt-processed in a Brabender single screw extruder as follows. The Aquasorb A500 was added to the extruder first, followed by the components of the hydrophobic phase, at a temperature of 130° C. The extruded hydrogel composition was placed onto a polyethylene terephthalate release liner and then pressed using a Carver press.

EXAMPLE 2

A second hydrogel composition (designated 12SP-38), comprised of a discontinuous hydrophobic phase and a discontinuous hydrophilic phase, was prepared containing the following components, using the melt extrusion process of Example 1:
Hydrophobic Phase:
Kalar 5215, 9.70 wt. %;
Styrene plasticizer, 29.12 wt. %;
SIS Vector 4111, 12.13 wt. %;
Regalite 1900, 9.70 wt. %;
Irganox 1010, 0.5 wt. %.
Hydrophilic Phase:
Aquasorb A500, 38.84 wt. %.

Examples 3 and 4 describe preparation of hydrogel compositions composed of a discontinuous hydrophobic phase and a continuous hydrophilic phase using melt extrusion.

EXAMPLE 3

A hydrogel composition (designated 12SP-42) comprised of a discontinuous hydrophobic phase and a continuous hydrophilic phase was prepared containing the following components:
Hydrophobic Phase:
Kalar 5246, 7.9 wt. %;
Styrene plasticizer, 23.70 wt. %;
SIS Vector 4111, 9.86 wt. %;
Regalite 1900, 7.90 wt. %;
Irganox 1010, 0.5 wt. %.
Hydrophilic Phase:
DOA, 3.94 wt. %;
CAB 551-0.2, 7.90 wt. %;
PVP/PEG 400, 38.35 wt. %.
The above components were melt-processed in a Brabender single screw extruder as follows. The CAB 551-0.2 and half of the PEG 400 were added to the extruder first, at a temperature of 140° C. Then, the PVP, the DOA, and the remaining PEG 400 were added at a temperature of 140° C. The extruded hydrogel composition was placed onto a polyethylene terephthalate (PET) release liner and then pressed using a Carver press.

EXAMPLE 4

A second hydrogel composition (designated 12SP-45) comprised of a discontinuous hydrophobic phase and a continuous hydrophilic phase was prepared containing the following components, using the melt extrusion process of Example 3:
Hydrophobic Phase:
Kalar 5246, 3.80 wt. %;
Kalar 5275, 3.80 wt. %;
Styrene plasticizer, 5.44 wt. %;
SIS Vector 6241, 19.60 wt. %;
Regalite 1900, 7.62 wt. %;
Irganox 1010, 0.5 wt. %.
Hydrophilic Phase:
DOA, 3.80 wt. %;
CAB 551-0.2, 7.62 wt. %;
PVP/PEG 400, 37 wt. %.

Examples 5-9 describe the preparation of hydrogel compositions composed entirely of a continuous hydrophilic phase using melt extrusion.

EXAMPLE 5

A hydrogel composition (designated 12SP-49) composed entirely of a continuous hydrophilic phase was prepared containing the following components:
CAB 551-0.2, 39.05 wt. %;
PVP (Kollidon 90), 27.17 wt. %;
PEG 400, 33.71 wt. %;
BHA, 0.077 wt. %.
The hydrogel composition was prepared using the melt extrusion procedure substantially as described in Example 1, as follows. The CAB 551-0.2 (20.202 g) and half of the PEG 400 (8.71 g) were added to the mixer first, at a temperature of 140° C. Then, a mixture of the PVP (14.055 g) and the remaining PEG 400 (8.71 g) were added to the CAB 551-0.2 melt at 130° C. After two minutes, the temperature went up to 148° C. The extruded hydrogel composition was placed on a polyethylene terephthalate release liner and was then pressed on a Carver press. The hydrogel composition obtained was flexible and translucent.

EXAMPLE 6

A hydrogel composition (designated 12SP-xx) composed entirely of a continuous hydrophilic phase was prepared containing the following components, using the melt extrusion procedure described in Example 1:
CAB 551-0.2, 21.96 wt. %;
PVP (Kollidon 90), 43.93 wt. %;
PEG 400, 33.71 wt. %.

EXAMPLE 7

A hydrogel composition (designated 12SP-46) composed entirely of a continuous hydrophilic phase was prepared containing the following components:
CAB 551-0.2, 45.92 wt. %;
PVP (Kollidon 90), 23.20 wt. %;
PEG 400, 30.88 wt. %.

The hydrogel composition was prepared using the melt extrusion procedure described in Example 1, with the following parameters:

TABLE 1

| Materials | Weight (g) | Temperature of melt (° C.) | Time of Addition | RPM |
|---|---|---|---|---|
| CAB 551-0.2 | 20.0 | 133 | 4:10 | 70 |
| PEG 400 | 10.45 | 133 | 4:16 | 70 |
| PVP | 10.10 | 140 | 4:21 | 117 |
| PEG 400 | 3.03 | 140 | 4:21 | 117 |

The CAB 551-0.2 and 10.45 g of the PEG 400 were added to the mixer first, followed by the PVP and 3.03 g of the PEG 400. The hydrogel composition was observed to lack adhesion, and was translucent.

EXAMPLE 8

A hydrogel composition (designated 12SP-47) composed entirely of a continuous hydrophilic phase was prepared containing the following components:
CAB 551-0.2, 45.92 wt. %;
PVP (Kollidon 90), 23.20 wt. %;
PEG 400, 30.88 wt. %.

The hydrogel composition was prepared using the melt extrusion procedure substantially as described in Example 1, as follows. The temperature of the melt was 139° C. during addition of the PVP (20.0 g) and half of the PEG 400 (7.77 g) to an initial mixture of the CAB 551-0.2 (10.0 g) and the remaining half of the PEG 400 (7.77 g). The melt was initially colorless, but a rise in temperature to 152° C. resulted in a yellowish hue.

EXAMPLE 9

A hydrogel composition (designated 12SP-48) composed entirely of a continuous hydrophilic phase was prepared containing the following components:
CAB 551-0.2, 32.175 wt. %;
PVP (Kollidon 90), 32.175 wt. %;
PEG 400, 35.65 wt. %.

The hydrogel composition was prepared using the melt extrusion procedure substantially as described in Example 1, as follows. The temperature of the melt was 139° C. 7during addition of the PVP (15.0 g) and half of the PEG 400 (8.81 g) to an initial mixture of the CAB 551-0.2 (15.0 g) and the remaining half of the PEG 400 (8.81 g).

Examples 10-17 describe the preparation of hydrogel compositions entirely composed of a continuous hydrophilic phase using solution casting.

EXAMPLE 10

A hydrogel composition (designated 12SP-30) composed entirely of a continuous hydrophilic phase was prepared containing the following components:
CAB 553-0.4, 32.0 wt. %;
PVC, 20.19 wt. %;
PEG 400, 7.08 wt. %.

The hydrogel composition was prepared using a solution casting process, as follows. The above components were combined in ethanol to provide a solution having a concentration of about 45%. The admixture was cast onto a polyethylene terephthalate release liner to provide a film about 0.40 mm thick. The coated release liner was then baked for two hours at a temperature of 90° C.

EXAMPLE 11

A hydrogel composition (designated 12SP-31-2) composed entirely of a continuous hydrophilic phase was prepared containing the following component, using a solution casting process as described in Example 10:
CAB 553-0.4, 30.11 wt. %;
PVCap, 20.0 wt. %;
PEG 400, 7.42 wt. %.

EXAMPLE 12

A hydrogel composition (designated 12SP-31-3) composed entirely of a continuous hydrophilic phase was prepared containing the following components, using a solution casting process as described in Example 10:
CAB 553-0.4, 25.40 wt. %;
PVCap, 20.31 wt. %;
PEG 400, 7.02 wt. %.

EXAMPLE 13

A hydrogel composition (designated 12SP-32-4) composed entirely of a continuous hydrophilic phase was prepared containing the following components, using a solution casting process as described in Example 10:
CAB 553-0.4, 20.51 wt. %;
PVCap, 20.13 wt. %;
PEG 400, 7.0 wt. %.

EXAMPLE 14

A hydrogel composition (designated 12SP-50A) composed entirely of a continuous hydrophilic phase was prepared containing the following components:
CAP 504-02, 20 g of a 40% (w/v) solution in ethanol;
CAB 553-04, 8 g of a 30% (w/v) solution in ethanol;
PVCap, 20 g of a 40% (w/v) solution in ethanol;
PEG 400, 7.0 g;
Cab-O-Sil, 0.03 g.
Total weight: 55.03 g The hydrogel composition was prepared using a solution casting process as described in Example 10. Specifically, the CAP 504-02 solution was added to the PVCap solution and mixed. The PEG 400 was then added, followed by the CAB 553-04 and the Cab-O-Sil.

EXAMPLE 15

A hydrogel composition (designated 12SP-50B) composed entirely of a continuous hydrophilic phase was prepared containing the following components, using a solution casting process and the specific procedure described in Example 14. CAP 504-02, 20 g of a 40% (w/v) solution in ethanol;
CAB 553-04, 10 g of a 30% (w/v) solution in ethanol;
PVCap, 20 g of a 40% (w/v) solution in ethanol;
PEG 400, 7.0 g;
Cab-O-Sil, 0.03 g.
Total weight: 57.03 g

EXAMPLE 16

A hydrogel composition (designated 12SP-50C) composed entirely of a continuous hydrophilic phase was prepared containing the following components, using a solution casting process and the specific procedure described in Example 14. CAP 504-02, 20 g of a 40% (w/v) solution in ethanol;
CAB 553-04, 15 g of a 30% (w/v) solution in ethanol;
PVCap, 20 g of a 40% (w/v) solution in ethanol;
PEG 400, 7.0 g;
Cab-O-Sil, 0.03 g.
Total weight: 57.03 g

EXAMPLE 17

A hydrogel composition (designated 12SP-50D) composed entirely of a continuous hydrophilic phase was prepared containing the following components, using a solution casting process and the specific procedure described in Example 14. CAP 504-02, 20 g of a 40% (w/v) solution in ethanol;
CAB 553-04, 4 g of a 30% (w/v) solution in ethanol;
PVCap, 20 g of a 40% (w/v) solution in ethanol;
PEG 400, 7.0 g;
Cab-O-Sil, 0.03 g.
Total weight: 57.03 g

EXAMPLE 18

Four hydrogel compositions (designated 12-SP-104, 12-SP-113, 12-SP-115, and 12-SP-117) composed entirely of a continuous hydrophilic phase were prepared containing the following components, using a melt extrusion process as described in Example 3:

TABLE 2

| Formulation | Weight Percent | | |
| --- | --- | --- | --- |
| | PVP 90 | PEG 400 | Eudragit L100-55 |
| 12-SP-104 | 59.67 | 35.44 | 4.91 |
| 12-SP-113 | 56.31 | 35.47 | 8.22 |
| 12 SP-115 | 54.38 | 30.62 | 15 |
| 12-SP-117 | 56.7 | 35.53 | 7.76 |

EXAMPLE 19

Water Uptake Studies

Water uptake studies were conducted on samples of hydrogel compositions prepared in the preceding examples. Swell ratio and water uptake were calculated, and the degree of opacity or translucence was determined visually.

Procedure: Each sample was die-cut into circles 25 mm in diameter. The cross-sectional area of the hydrogel composition was measured using a ruler while the thickness of the patch was determined using a Mitotoyo Digimatic Micrometer at three points across the sample. The weight of the dry hydrogel composition was also determined using a 5-decimal point microbalance. Each hydrogel was then immersed in 20 mL of phosphate-buffered saline (0.9% w/v, 0.1M phosphate buffer pH 7.40) at 37° C. The weight and dimensions of each swollen hydrogel were determined at the times indicated in the tables below, after dabbing off excess solution. The weight difference represents the amount of water imbibed by the material. The patch was dried at 90° C. for 2 to 4 hours before taking its weight and dimensions to obtain the degree of dissolution of the patch. Each experiment was repeated three times, and the indicated values are averages. The time of each experiment varied from 15.5 to 72 hours. Results are set forth below.

Three hydrogel compositions were prepared as described in Example 3, designated 12SP-42A, 12SP-42B, and 12SP-42C. The results obtained after 15.5 hours were as follows:

TABLE 3

| | Water Gain and Loss | | | | | |
| --- | --- | --- | --- | --- | --- | --- |
| | Hydrogel composition | | | Water | | |
| Sample No. 12SP- | Initial Wt (g) | Final Wt (g) | Water Gain (g) | Initial Wt (g) | Final Wt (g) | Water Loss (g) |
| 42A | 0.537 | 0.995 | 0.458 | 18.739 | 17.751 | 0.988 |
| 42B | 0.550 | 1.031 | 0.481 | 18.491 | 17.135 | 1.356 |
| 42C | 0.560 | 1.130 | 0.570 | 18.383 | 17.288 | 1.095 |

TABLE 4

| | Thickness after water uptake | | | | |
| --- | --- | --- | --- | --- | --- |
| Sample No. 12SP- | Initial Thickness (mm) | Final Thickness (mm) | Initial Diameter (mm) | Final Diameter | Dry Wt after water uptake (g) |
| 42A | 0.92 | 2.07 | 25 | 26 | 0.342 |
| 42B | 0.97 | 2.10 | 25 | 25 | 0.354 |
| 42C | 0.95 | 2.31 | 25 | 26 | 0.360 |

TABLE 5

| Swell Ratio and % Water Uptake | | |
| --- | --- | --- |
| Sample No. 12SP-. | Swell Ratio | Water Uptake % |
| 42A | 2.91 | 85.29 |
| 42B | 2.91 | 87.45 |
| 42C | 3.13 | 101.78 |
| Average | 2.98 | 91.50 |
| σ | 0.127 | 8.96 |
| % RSD | 4.26 | 9.8 |

During swelling, the hydrogel compositions took on a white color immediately, and after 16 hours of swelling some yellow became visible. After drying, all hydrogels were translucent and relatively brittle.

The average values of various swelling-related parameters obtained for 12SP-42A, -42B, and -42C are set forth in Table 6:

TABLE 6

| Parameter | Value | RSD % |
|---|---|---|
| Average dry weight (g) | 0.352 | 2.60 |
| Average wet weight (g) | 1.052 | 6.60 |
| Weight of water absorbed | 1.05 | 6.66 |
| Water absorbed/unit area of film (g/cm$^{-2}$) | 0.223 | 21.44 |
| Water absorption capacity $^a$ (swell ratio) | 2.98 | 4.26 |
| % Increase in surface area | 2.66 | 0.86 |
| % Increase in thickness | 128.21 | 10.61 |
| % Water uptake | 91.5 | 9.8 |

$^a$ Water absorption capacity is defined as the weight ratio of water absorbed to the dried film.

The hydrogel compositions of Examples 5, 6, 7, and 8 were evaluated after 24 hours, with the following results:

TABLE 7

| | Swell ratio | | Water Uptake | |
|---|---|---|---|---|
| Hydrogel No./Example No. | Average N = 3 | % RSD | Average N = 3 | % RSD |
| 12SP-46/Ex. 8 | 1.42 | 2.54 | 36.16 | 4.18 |
| 12SP-47/Ex. 7 | 4.63 | 1.96 | 184.0 | 36.80 |
| 12SP-48/Ex. 9 | 2.98 | 4.26 | 91.5 | 9.8 |
| 12SP-49/Ex. 5 | 2.09 | 26.62 | 79.9 | 21.5 |

TABLE 8

| Hydrogel No./Example No. | Observation After Water Uptake |
|---|---|
| 12SP-46/Ex. 8 | White; no adhesion |
| 12SP-47/Ex. 7 | White; no adhesion |
| 12SP-48/Ex. 9 | White; no adhesion |
| 12SP-49/Ex. 5 | Translucent; no adhesion |

The hydrogel compositions of Examples 10 through 13 were evaluated after 20 hours, with the following results:

TABLE 9

| | Swell ratio | | Water Uptake | |
|---|---|---|---|---|
| Hydrogel No./Example No. | Average N = 3 | % RSD | Average N = 3 | % RSD |
| 12SP30/Ex. 10 | 4.68 | 9.19 | 37.4 | 24.38 |
| 12SP31-2/Ex. 11 | 5.27 | 11.76 | 40.0 | 37.50 |
| 12SP31-3/Ex. 12 | 6.60 | 16.06 | 42.36 | 17.80 |
| 12SP32-4/Ex. 13 | 9.80 | 16.8 | 52.0 | 15.11 |

TABLE 10

| Hydrogel No./Example No. | Observation After Water Uptake |
|---|---|
| 12SP30/Ex. 10 | Translucent; no adhesion |
| 12SP31-2/Ex. 11 | Translucent; no adhesion |
| 12SP31-3/Ex. 12 | Translucent; no adhesion |
| 12SP32-4/Ex. 13 | Translucent; no adhesion |

The hydrogel compositions of Examples 14 through 16 were evaluated after 22 hours, with the following results:

TABLE 11

| | Swell ratio | | Water Uptake | |
|---|---|---|---|---|
| Hydrogel No./Example No. | Average N = 3 | % RSD | Average N = 3 | % RSD |
| 12SP50A/Ex. 14 | 3.50 | 16.57 | 56.32 | 32.38 |
| 12SP50B/Ex. 15 | 3.45 | 8.67 | 44.66 | 29.35 |
| 12SP50C/Ex. 16 | 3.12 | 25.0 | 59.14 | 57.0 |

TABLE 12

| Hydrogel No./Example No. | Observation After Water Uptake |
|---|---|
| 12SP50A/Ex. 14 | Translucent; no adhesion |
| 12SP50B/Ex. 15 | Translucent; no adhesion |
| 12SP50C/Ex. 16 | Opaque; no adhesion |

Three samples of each of the four hydrogel compositions of Example 18 were evaluated after one hour with the following results:

TABLE 13

| | Water Uptake After One Hour | | | | | |
|---|---|---|---|---|---|---|
| | | SCA | | | WATER | |
| SAMPLE | Initial Wt. | Final Wt. | Water Gain | Initial Wt. | Final Wt. | Water Loss |
| 12-SP-104-1 | 0.303 | 3.136 | 2.833 | 15.01 | 11.544 | 3.466 |
| 12-SP-104-2 | 0.237 | 3.39 | 3.153 | 15.072 | 10.986 | 4.086 |
| 12-SP-104-3 | 0.27 | 2.792 | 2.522 | 15.02 | 11.396 | 3.624 |
| 12-SP-113-1 | 0.229 | 2.459 | 2.23 | 15.97 | 12.765 | 3.205 |
| 12-SP-113-2 | 0.228 | 2.678 | 2.45 | 15.772 | 12.607 | 3.165 |
| 12-SP-113-3 | 0.217 | 2.58 | 2.363 | 15.971 | 12.801 | 3.17 |
| 12-SP-115-1 | 0.184 | 1.062 | 0.878 | 15.947 | 14.203 | 1.744 |
| 12-SP-115-2 | 0.177 | 1.032 | 0.855 | 15.527 | 13.687 | 1.84 |
| 12-SP-115-3 | 0.163 | 0.875 | 0.712 | 15.273 | 13.793 | 1.48 |
| 12-SP-117-1 | 0.122 | 1.466 | 1.344 | 14.541 | 12.403 | 2.138 |
| 12-SP-117-2 | 0.122 | 1.433 | 1.311 | 14.11 | 11.889 | 2.221 |
| 12-SP-117-3 | 0.115 | 1.247 | 1.132 | 14.732 | 12.723 | 2.009 |

TABLE 14

| | Thickness After Water Uptake for One Hour | | | | |
|---|---|---|---|---|---|
| Sample no. | Initial Thickness (mil) | Final Thickness (mil) | Initial Diameter (mil) | Final Diameter (mil) | Dry wt. after Water Uptake (g) |
| 12-SP-104-1 | 20.1 | — | 984.25 | 1750 | 0.262 |
| 12-SP-104-2 | 16.9 | — | 984.25 | 1750 | 0.147 |
| 12-SP-104-3 | 16.9 | — | 984.25 | 1750 | 0.178 |
| 12-SP-113-1 | 14 | 22 | 984.25 | 1750 | 0.134 |
| 12-SP-113-2 | 14.5 | 23.5 | 984.25 | 1750 | 0.14 |
| 12-SP-113-3 | 14 | 27.5 | 984.25 | 1750 | 0.136 |
| 12-SP-115-1 | 11.5 | 25.99 | 984.25 | 1750 | 0.126 |
| 12-SP-115-2 | 11.5 | 24.99 | 984.25 | 1750 | 0.144 |
| 12-SP-115-3 | 10 | 23.5 | 984.25 | 1750 | 0.08 |
| 12-SP-117-1 | 7.5 | 9 | — | — | — |
| 12-SP-117-2 | 8.5 | 10.5 | — | — | — |
| 12-SP-117-3 | 8.5 | 8.5 | — | — | 0.066 |

TABLE 15

Swell Ratios after Water Uptake for One Hour

| Sample | Swell Ratio | Water Uptake (%) |
|---|---|---|
| SP-104-1 | 11.969 | 934.98 |
| SP-104-2 | 23.06 | 1330.38 |
| SP-104-3 | 19.045 | 934.07 |
| Average | 18.024 | 1066.47 |
| % RSD | 31.15 | 21.43 |
| SP-113-1 | 18.35 | 873.8 |
| SP-113-2 | 19.13 | 1074.56 |
| SP-113-3 | 18.97 | 1088.94 |
| Average | 18.81 | 1012.43 |
| % RSD | 2.19 | 11.88 |
| SP-115-1 | 8.43 | 477.17 |
| SP-115-2 | 7.16 | 483.05 |
| SP-115-3 | 10.94 | 436.81 |
| Average | 8.84 | 465.67 |
| % RSD | 21.76 | 5.4 |
| SP-117-1 | 19.81 | 1101.64 |
| SP-117-2 | — | 1074.6 |
| SP-117-3 | 18.89 | 984.35 |
| Average | 19.35 | 1053.53 |
| % RSD | 3.36 | 5.83 |

EXAMPLE 20

Wear Studies

The solution-cast hydrogel compositions prepared in Examples 10-13 were applied to the skin of three individuals, on the back of the hand. The individuals were asked to rate (1) initial tack, (2) continuing adhesion, (3) edge lift, (4) comfort, (5) cold flow, and (6) residual upon removal, on a scale of 1 to 5, with 1=poor, 2=fair, 3=good, 4=very good, and 5=excellent. The results of the test, averaged among the three individuals, are set forth in Table 16:

TABLE 16

| Hydrogel #/ Example # | Initial Tack | Continued adhesion | Edge lift | Comfort | Cold Flow | Residual |
|---|---|---|---|---|---|---|
| 12SP-30/ Ex. 10 | 4 | 4 | 4.5 | 4.5 | 4.5 | 3.5 |
| 12SP31-2/ Ex. 11 | 5 | Over 24 hours | 5 | 5 | 5 | 5 |
| 12SP31-3/ Ex. 12 | 5 | Over 6 hours | Notice cracking | 5 | 5 | 5 |
| 12SP32-4/ Ex. 13 | 5 | 2 hours | 5 | 5 | 5 | 5 |

We claim:

1. A hydrogel composition comprised of a single discontinuous hydrophobic phase and a discontinuous hydrophilic phase, wherein the discontinuous hydrophobic phase comprises (I) polyisobutylene, (II) a plasticizer, (iii) a tackifying resin, and (iv) an optional antioxidant, and the/discontinuous hydrophilic phase consists of one or more hydrophilic polymers.

2. The hydrogel composition of claim 1, wherein the hydrophilic phase consists of a crosslinked hydrophilic polymer, and particles of the crosslinked hydrophilic polymer are dispersed in the hydrophobic phase.

3. The hydrogel composition of claim 2, wherein the crosslinked hydrophilic polymer is a crosslinked cellulosic polymer.

4. The hydrogel composition of claim 3, wherein the crosslinked cellulosic polymer is crosslinked sodium carboxymethylcellulose.

5. The hydrogel composition of claim 3, wherein the crosslinked cellulosic polymer is selected from crosslinked sodium carboxymethylcellulose (CMC), crosslinked hydroxyethyl cellulose (HEC), and crosslinked partial free acid CMC.

6. The hydrogel composition of claim 1, wherein the plasticizer is a low molecular weight plasticizer selected from the group consisting of dialkyl phthalates, dicycycloalkyl phthalates, diaryl phthalates, mixed alkyl-aryl phthalates, alkyl phosphates, aryl phosphates, alkyl citrates, citrate esters, alkyl adipates, dialkyl tartrates, dialkyl sebacates, dialkyl succinates, alkyl glycolates, alkyl glycerolates, glycol esters, glycerol esters, styrene-based copolymers, and mixtures thereof.

7. The hydrogel composition of claim 6, wherein the low molecular weight plasticizer is selected from the group consisting of dimethyl phthalate, diethyl phthalate, dipropyl phthalate, di(2-ethylhexyl)phthalate, di-isopropyl phthalate, diamyl phthalate, dicapryl phthalate, tributyl phosphate, trioctyl phosphate, tricresyl phosphate, triphenyl phosphate, trimethyl citrate, triethyl citrate, tributyl citrate, acetyl triethyl citrate, trihexyl citrate, dioctyl adipate, diethyl adipate, di(2-methylethyl)adipate, dihexyl adipate, diethyl tartrate, dibutyl tartrate, diethyl sebacate, dipropyl sebacate, dinanyl sebacate, diethyl succinate, dibutyl succinate, glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate, triethylene glycol dipropionate, and mixtures thereof.

8. The hydrogel composition of claim 7, wherein the low molecular weight plasticizer is dioctyl adipate.

9. The hydrogel composition of claim 1, wherein the optional antioxidant is present In an amount of up to about 2% by weight.

10. The hydrogel composition of claim 9, wherein the antioxidant is a sterically hindered phenol.

11. The hydrogel composition of claim 1, further including an active agent.

12. The hydrogel composition of claim 1, further including at least one additive selected from the group consisting of fillers, preservatives, pH regulators, softeners, thickeners, pigments, dyes, refractive particles, stabilizers, toughening agents and detackifiers.

13. A method of forming a hydrogel, the method comprising:
    mixing the components of a discontinuous hydrophobic phase comprising polyisobutylene, a plasticizing elastomer, a tackifying resin, and an optional antioxidant, with the components of a discontinuous hydropcophilic phase consisting of one or more hydrophilic polymers, to thereby form a hydrogel composition comprising a single discontinuous hydrophobic phase and a discontinuous hydrophilic phase.

14. The method of claim 13, wherein the mixing is carried out at a temperature from about 90° C. to about 140° C.

15. The method of claim 14, further comprising melt processing the components of the hydrophobic and hydrophilic phases through an extruder.

16. A melt-extruded hydrogel composition of claim 1.

17. The hydrogel composition of claim 1 comprising about 5 weight percent to 15 weight percent polyisobutylene, based upon the composition in dry form.

18. The hydrogel composition of claim 1, comprising from about 5 weight percent to about 15 weight percent tackifying resin, based upon the composition in dry form.

19. The hydrogel composition of claim 1, wherein the weight ratio of tackifying resin to hydrophobic polymer ranges from 40:60 to 60:40.

20. The hydrogel composition of claim 2, comprising about 25 weight percent to 65 weight percent crosslinked hydrophilic polymer, based upon the composition in dry form.

21. The hydrogel composition of claim 1, comprising from about 25 weight percent to 40 weight percent plasticizer after drying.

22. The hydrogel composition of claim 1, comprising from about 5 weight percent to 15 weight percent polyisobutylene, from about 25 weight percent to 65 weight percent hydrophilic polymer, from about 25 weight percent to 40 weight percent plasticizer, and from about 5 weight percent to about 15 weight percent tackifying resin, based upon the composition in dry form.

* * * * *